(12) United States Patent
Freer et al.

(10) Patent No.: US 8,530,720 B2
(45) Date of Patent: Sep. 10, 2013

(54) THERMALLY CONDUCTIVE, METAL-BASED BANDAGES TO AID IN MEDICAL HEALING AND METHODS OF USE

(75) Inventors: Carl J. Freer, Aspen, CO (US); Ericka S. Freer, Aspen, CO (US); Terrence M. Wyles, Aurora, CO (US)

(73) Assignee: Aluminaid International AG, Sursee (CH)

( * ) Notice: Subject to any disclaimer, the term of this patent is extended or adjusted under 35 U.S.C. 154(b) by 0 days.

(21) Appl. No.: 13/548,055

(22) Filed: Jul. 12, 2012

(65) Prior Publication Data

US 2013/0030341 A1 Jan. 31, 2013

Related U.S. Application Data

(63) Continuation of application No. PCT/US2012/046310, filed on Jul. 11, 2012, and a continuation-in-part of application No. PCT/US2011/067256, filed on Dec. 23, 2011.

(60) Provisional application No. 61/670,090, filed on Jul. 10, 2012, provisional application No. 61/513,366, filed on Jul. 29, 2011.

(51) Int. Cl.
*A61F 15/00* (2006.01)

(52) U.S. Cl.
USPC ............................................. 602/58; 602/43

(58) Field of Classification Search
USPC .......... 602/1–2, 41–43, 48, 58; 424/443–447
See application file for complete search history.

(56) References Cited

U.S. PATENT DOCUMENTS

| | | |
|---|---|---|
| 2,577,945 A | 12/1951 | Starr |
| 3,596,657 A | 8/1971 | Eidus |

(Continued)

FOREIGN PATENT DOCUMENTS

| | | |
|---|---|---|
| KR | 20-0394032 Y1 | 9/2005 |
| WO | WO9303691 | 3/1993 |

(Continued)

OTHER PUBLICATIONS

"Local application of aluminum foil and other substances in burn therapy", Original Research Article, The American Journal of Surgery, vol. 76, Issue 5, Nov. 1948, 594604 W.A. Brown, A.W. Farmer, W.R. Franks.

(Continued)

*Primary Examiner* — Patricia Bianco
*Assistant Examiner* — Camtu Nguyen

(57) ABSTRACT

The inventive disclosure contained herein is generally directed to a class of medical bandages that in many embodiments are effective in the treatment of various types of tissue burns, whether be burns due to thermal burns, sun exposure, or rashes. Such products can include a plurality of specialized bandages and wraps that incorporate an extremely thin layer of thermally conductive metal (often aluminum) at the base of a substrate adapted to be in direct contact with a burn wound, while manufacturing the top side of the aluminum substrate to have a heat-dissipation-enhancing topography to help cool burns faster by enhancing thermal-convection properties. The bandage can also feature a thermochromic indicator for users to realize the thermal-cooling status of a burn to which a bandage has been applied.

11 Claims, 25 Drawing Sheets

(56) References Cited

U.S. PATENT DOCUMENTS

| | | | |
|---|---|---|---|
| 3,597,976 | A | 8/1971 | Fryar |
| 4,139,004 | A | 2/1979 | Gonzalez |
| D252,136 | S | 6/1979 | Khemka |
| 4,181,127 | A | 1/1980 | Linsky |
| D281,147 | S | 10/1985 | Khemka |
| 5,309,925 | A * | 5/1994 | Policastro .................. 128/849 |
| 5,403,588 | A | 4/1995 | Santa Ana |
| 5,529,784 | A | 6/1996 | DiPippo |
| 5,730,721 | A | 3/1998 | Hyatt |
| 6,164,279 | A | 12/2000 | Tweedle |
| 6,270,783 | B1 | 8/2001 | Slavcheff |
| 6,464,672 | B1 | 10/2002 | Buckley |
| 6,522,918 | B1 * | 2/2003 | Crisp et al. .................. 604/20 |
| 6,623,835 | B2 | 9/2003 | Chang |
| 7,264,602 | B1 | 9/2007 | Longsworth |
| 7,625,117 | B2 | 12/2009 | Haslett |
| 7,721,349 | B1 | 5/2010 | Strauss |
| 7,837,637 | B2 | 11/2010 | Halanski |
| 2007/0185467 | A1 | 8/2007 | Klofta |
| 2007/0270925 | A1 | 11/2007 | Levinson |
| 2008/0064997 | A1 | 3/2008 | Flick |
| 2008/0306407 | A1 | 12/2008 | Taylor |
| 2009/0204100 | A1 | 8/2009 | Van Pieterson |
| 2010/0069813 | A1 | 3/2010 | Crisp |
| 2011/0046581 | A1 | 2/2011 | Linder |
| 2011/0082406 | A1 | 4/2011 | Halanski |
| 2011/0275978 | A1 | 11/2011 | Hyde |

FOREIGN PATENT DOCUMENTS

| | | |
|---|---|---|
| WO | WO0074616 | 12/2000 |
| WO | WO2005028984 | 3/2005 |
| WO | WO2006048879 | 5/2006 |
| WO | WO2007125439 | 11/2007 |
| WO | WO2009111537 | 9/2009 |

OTHER PUBLICATIONS

"Aluminium foil as a wound dressing", British Journal of Plastic Surgery, vol. 32, Issue 2, Apr. 1979, 145146, M.D. Poole, A.M. Kalus, Dr. med. H. von Domarus.

"Additional uses of aluminum foil in the treatment of burns", Original Research Article, The American Journal of Surgery, vol. 101, Issue 4, Apr. 1961, 428430, John L. Terry, John C. Trabue.

International Search Report for PCT Application No. PCT/US2012/046310 (from the Korean ISA, dated Jan. 28, 2013.

Written Opinion on Patentability for PCT Application No. PCT/US2012/046310 (from the Korean ISA, dated Jan. 28, 2013.

"Medicine: Foil for Burns", Time Magazine, Aug. 30, 1948; available at http://www.time.com/time/magazine/article/0,9171,799094,00.html (last accessed on Jul. 4, 2012).

International Search Report for PCT Application No. PCT/US2011/067256 (from the Korean ISA, dated Sep. 26, 2012.

Written Opinion on Patentability for PCT Application No. PCT/US2011/067256 (from the Korean ISA, dated Sep. 26, 2012.

* cited by examiner

TOP

BOTTOM

TOP

BOTTOM

SECTION A-A; SCALE 100 : 1

Size A

Size B

Size C

Size D

THERMALLY CONDUCTIVE, METAL-BASED BANDAGES TO AID IN MEDICAL HEALING AND METHODS OF USE

CROSS-REFERENCE TO RELATED APPLICATIONS

The present patent application is a Continuation-In-Part of, and claims the benefit of Patent Cooperation Treaty (PCT) Application No. PCT/US2011/67256, filed on Dec. 23, 2011, for "Aluminum-Based Bandages to Aid in Medical Healing and Methods of Use".

The present patent application also claims the benefit of Patent Cooperation Treaty (PCT) Application No. PCT/US2012/46310, filed on Jul. 11, 2012, for "Thermally Conductive, Metal-Based Bandages to aid in Medical healing and Methods of Use".

The present patent application also claims the benefit of U.S. Patent Application No. 61/513,366, filed on Jul. 29, 2011, for "Aluminum-Infused Compositions and Devices to Aid in Medical Healing and Methods of Use".

The present patent application also claims the benefit of U.S. Patent Application No. 61/670,090, filed on Jul. 10, 2012, for "Thermally Conductive, Metal-Based Bandages to Aid in Medical Healing and Methods of Use".

In addition, the present patent application hereby incorporates by reference PCT Application No. PCT/US2011/67256, Patent Cooperation Treaty Application No. PCT/US2012/46310, U.S. Patent Application No. 61/513,366, and U.S. Patent Application No. 61/670,090, each in their entirety for all purposes.

BACKGROUND

Burn injuries are caused by fire, chemicals, electricity, and friction and can vary in severity. First degree burns are the least severe, causing redness, and healing relatively quickly. On the other end of the spectrum, fourth degree burns are the most severe, burning down to the level of the muscle and bone. Second and third degree burns fall between these extremes.

Medical professionals often try to strike a balance when deciding how to treat burns. On one hand, if a burn is superficial and relatively dry, then many feel that the wound should be kept moist with water or some sort of ointment or cream. For example, Dr Xu of China National has developed an "alternative" technique called Moist Exposed Burn Therapy, which, unlike the conventional way to heal a burn victim by keeping the burn wound dry, Professor Xu keeps the patient's burn wound moist. Dr. Xu's treatment regimen requires very little administration of antibiotics and disinfectants to the burn wound. Instead, Dr. Xu uses natural herbs to aid burn-wound healing, wherein natural-plant extracts at the base of a beeswax is the main ingredient used. However, a problem with applying many ointments and/or creams is that such applications often do not help draw heat away from a wound. On the other hand, if a burn is more serious, such as a second-degree burn that is oozing fluid, then there is an enhanced fear of infection. In such cases, some medical professionals feel that such wounds should be kept relatively dry, while still others may advocate for the application of various ointment dressings with antibiotic properties to fight infection. Hence, it would be desirable to come up with a treatment strategy that is able to provide the best of all worlds.

On Aug. 30, 1948, *Time Magazine* reported that steam from an exploding locomotive had scalded Fireman Frank Mihlan of the Erie Railroad. When Mihlan was carried into Cleveland's Charity Hospital on Jul. 15, 1948, 70% of his body was burned, and doctors thought that Mihlan had little chance of survival. However, attending surgeons decided to try wrapping the Mihlan's burns in thin strips of aluminum foil, a technique developed by Toronto's Dr. Alfred W. Farmer. It was the first time that aluminum foil for burns had been used in the U.S.; the first time it had ever been used for burns of the whole body. Relief from pain was "miraculous", and within 20 minutes of application, Mihlan was resting comfortably. As an added precaution, Mihlan was given intravenous fluids and penicillin. The aluminum foil, which looked like the inside wrapping of a cigarette package, apparently acted as a seal for the body fluids that seep from burned surfaces. It also apparently helped kill bacteria, speeding the healing process. Twelve days after being bandaged in the aluminum foil wrappings, Mihlan was out of bed. Eventually, Mihlan left the hospital unscarred, albeit temporarily reddened.

Further, a 2004 *American Journal* article reported:

Aluminum foil as a dry sterile initial covering for thermal burns under occlusive pressure dressings has been presented as a method of diminishing the maceration of a burn surface. The method appeared to influence favorably the local result by elimination of the use of ointments and by facilitating the dispersion of exudate to the periphery of the burn. No evidence of toxicity as a result of the treatment was found. The systemic reaction was, if anything, less obvious.

Despite the above-mentioned anecdotal report and the reported research, public data is not readily accessible in-relation to the practicable applications of using aluminum foil as a healing agent. In addition, to date, there appears to be no commercially designed aluminum-derived medical products for general-purpose sale other than large blankets usually reserved for Emergency-Services organizations.

One existing known use for aluminum-derived products is in the employment of the astringent aluminum-based compound, aluminum chloride, which has been used in various concentrations in the art to apply to deodorant pads in order to cause constriction of sweat pores. For example, U.S. Pat. No. 5,403,588 to Santa Ana is directed to a disposable body deodorant pad and deodorant preparation therefor. The Santa Ana Patent basically dissolves 3 to 4 grams of aluminum chloride into about 130 cc of an acetone-isopropyl alcohol solution to achieve an effective constriction of the user's sweat pores. Despite this known use, there are no aluminum-based compositions of matter available on the market for acting as a styptic or otherwise sealing a wound.

Ostensibly, there simply is no specific product range available to the general public that employs both the natural and by-product medical advantages of aluminum. For example, there are no bandages on the market that are comprised of extremely thin aluminum layers or strips, and nor are there therapeutic creams, ointments, or other medicinal compositions that are infused with molecular compositions that substantially include aluminum.

It would be advantageous to develop a set of aluminum-infused healing/therapeutic products (e.g., specialized bandages, burn creams, etc.) that are easy for a consumer to safely use.

BRIEF SUMMARY

The inventive disclosure contained herein is generally directed to a class of medical products that in many embodiments are effective in the treatment of tissue burns, whether be burns due to thermal burns, sun exposure, or rashes. Such products can include a plurality of specialized bandages and wraps that incorporate an extremely thin layer of a thermally conductive metal with enhanced material and surface features to ensure flexibility and effective heat-transfer characteristics to cool a burn wound. One key embodiment employing an enhanced heat-dissipation capability features a this aluminum substrate, with one side adapted to make direct contact with a burn wound, while the other side of the aluminum substrate exposes to the air a topography that resembles a microscopic field of cones, hollowed and also providing aeration to the wound. The hollowed cone structures provide a greatly increased exposed surface area of the aluminum substrate to encourage efficient thermal convection processes, while still allowing the bandage to flex in any needed direction. Besides exhibiting multiple properties that are beneficial to healing certain types of tissue wounds, as discussed infra, aluminum is non-toxic, easy to sterilize, relatively inexpensive and easy to fabricate with, and abundantly mined worldwide.

Hereinafter, the overall class of products described in this patent application is referred to as "Aluminaid™" or "Aluminaids™". These aluminum-derived products are specifically designed to alleviate the discomfort and pain caused by thermal burns. Additionally, Aluminaids™, through a combination of natural composition and the prevailing production processes, inherit the potential to minimize scarring, inhibit infection, prevent maceration, and reduce the necessity for later skin grafting.

The inventive principles and disclosures provided in this patent application can be applied to any thermally conductive metal-based substrate, and as such are contemplated as being included within the scope of this patent application, including the appended claims.

The forgoing Brief Summary is provided as a convenient overview of a few key (but not all) embodiments; however, it is not intended to limit the scope of the disclosures contained within this patent application, including the appended claims and accompanying drawings.

BRIEF DESCRIPTION OF THE DRAWINGS

This patent application is a Continuation-In-Part of, and incorporates by reference, Patent Cooperation Treaty (PCT) Application No. PCT/US2011/67256, filed on Dec. 23, 2011, for "Aluminum-Based Bandages to Aid in Medical Healing and Methods of Use". However, for convenience and clarity for the reader, original FIGS. 1A-19 from PCT Application No. PCT/US2011/67256 are repeated in the present patent application. However, FIGS. 20A-31G, which depict some additional and/or refined embodiments, have been added to the disclosure. Brief descriptions for all of the figures are as follows:

FIG. 5A depicts one embodiment of an Aluminaid™ bandage (finger-form-factor), showing the top-side topography that features a field of heat-dissipation-enhancing cone-like protrusions. This form factor includes an end adhesive tab 35 adapted to engage the end of a finger, and three incrementally sized sections 20, 25, 30 for engaging an associated region of a finger the bandage is applied to.

FIG. 5B depicts one embodiment of an Aluminaid™ bandage (narrow finger-form-factor), showing the bottom-side topography that features a substantially smooth aluminum substrate, which is intended to make contact with a user's tissue. This form factor includes an end adhesive tab 35 adapted to engage the end of a finger, and three incrementally sized sections 20, 25, 30 for engaging an associated region of a finger the bandage is applied to.

FIG. 6A depicts one embodiment of an Aluminaid™ bandage (finger-form-factor), showing the top-side topography that features a field of heat-dissipation-enhancing pyramid-like protrusions. This form factor includes an end adhesive tab 35 adapted to engage the end of a finger, and three incrementally sized sections 20, 25, 30 for engaging an associated region of a finger the bandage is applied to.

FIG. 6B depicts one embodiment of an Aluminaid™ bandage (narrow finger-form-factor), showing the bottom-side topography that features a substantially smooth aluminum substrate, which is intended to make contact with a user's tissue. This form factor includes an end adhesive tab 35 adapted to engage the end of a finger, and three incrementally sized sections 20, 25, 30 for engaging an associated region of a finger the bandage is applied to.

DETAILED DESCRIPTION

I. Introduction

Figure 1A:
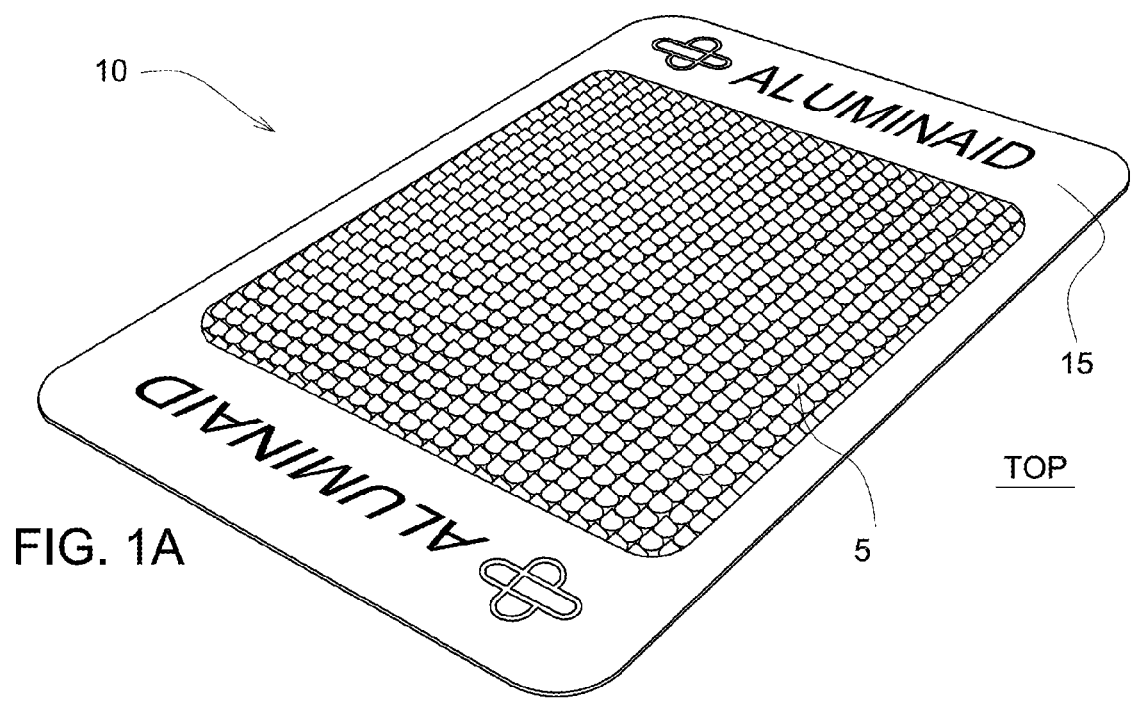
FIG. 1A depicts one embodiment of an Aluminaid™ bandage (large-rectangular general form factor), showing the top-side topography that features a field of heat-dissipation-enhancing cone-like protrusions.
Figure 1B:
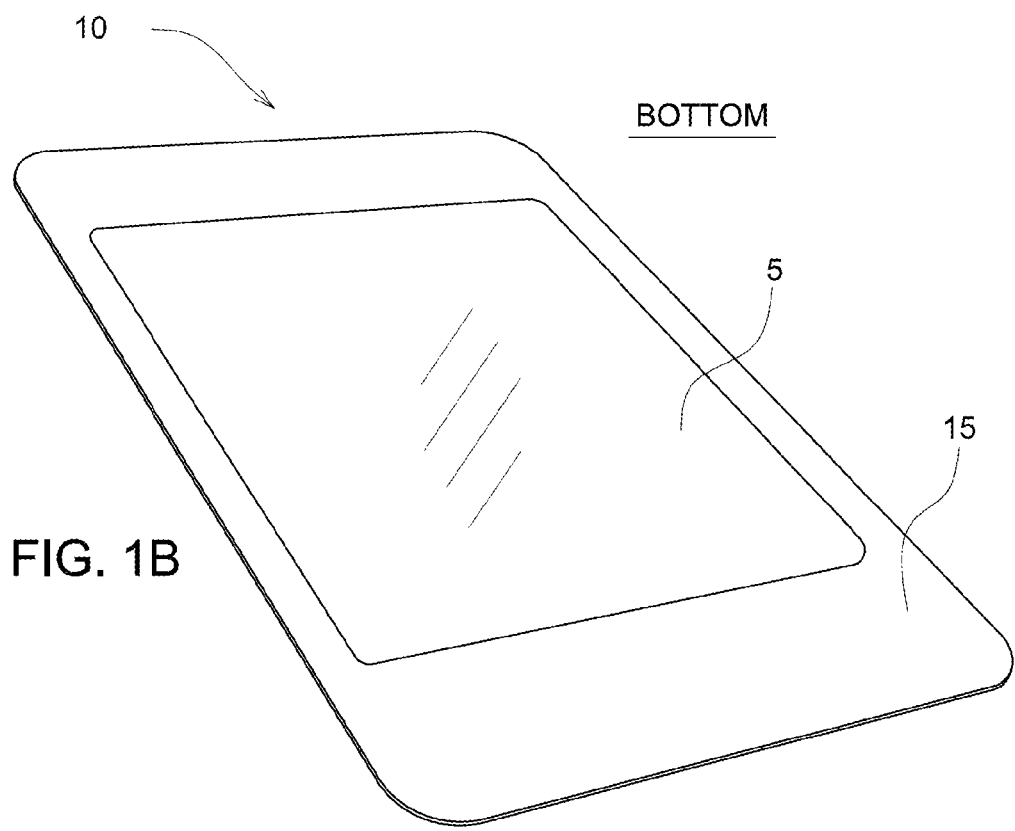
FIG. 1B depicts one embodiment of an Aluminaid™ bandage (large-rectangular general form factor), showing the bottom-side topography that features a substantially smooth aluminum substrate, which is intended to make contact with a user's tissue.
Figure 2A:
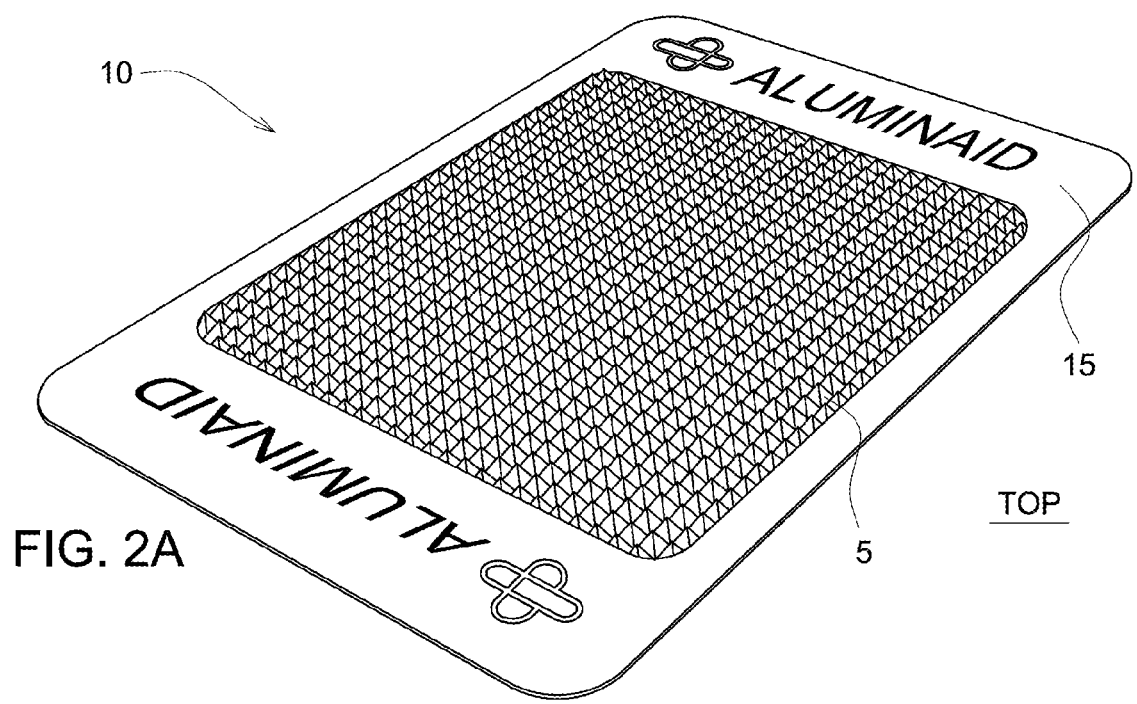
FIG. 2A depicts one embodiment of an Aluminaid™ bandage (large-rectangular general form factor), showing the top-side topography that features a field of heat-dissipation-enhancing pyramid-like protrusions.
Figure 2B:
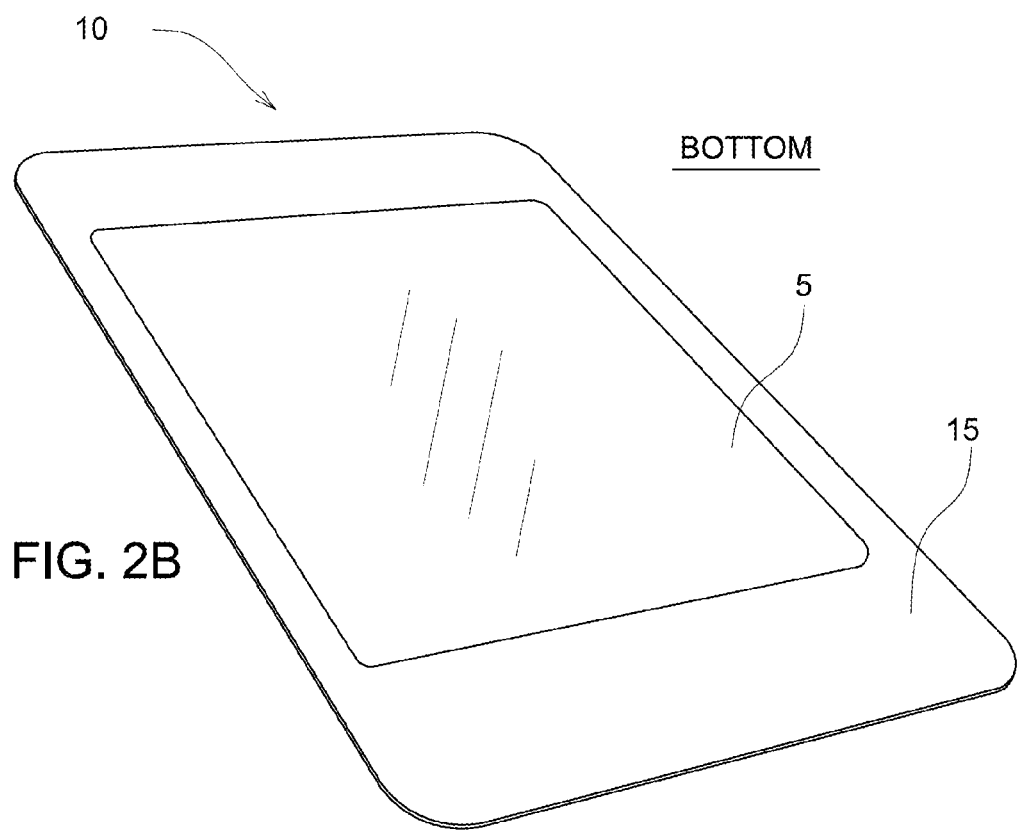
FIG. 2B depicts one embodiment of an Aluminaid™ bandage (large-rectangular general form factor), showing the bottom-side topography that features a substantially smooth aluminum substrate, which is intended to make contact with a user's tissue.
Figure 3A:
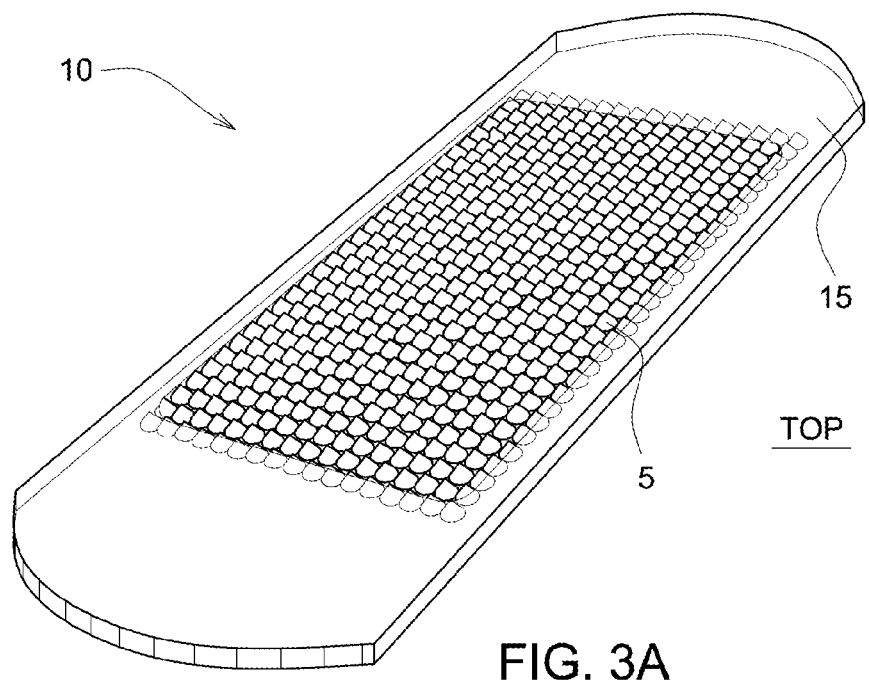
FIG. 3A depicts one embodiment of an Aluminaid™ bandage (narrow, substantially rectangular general form factor), showing the top-side topography that features a field of heat-dissipation-enhancing cone-like protrusions.
Figure 3B:
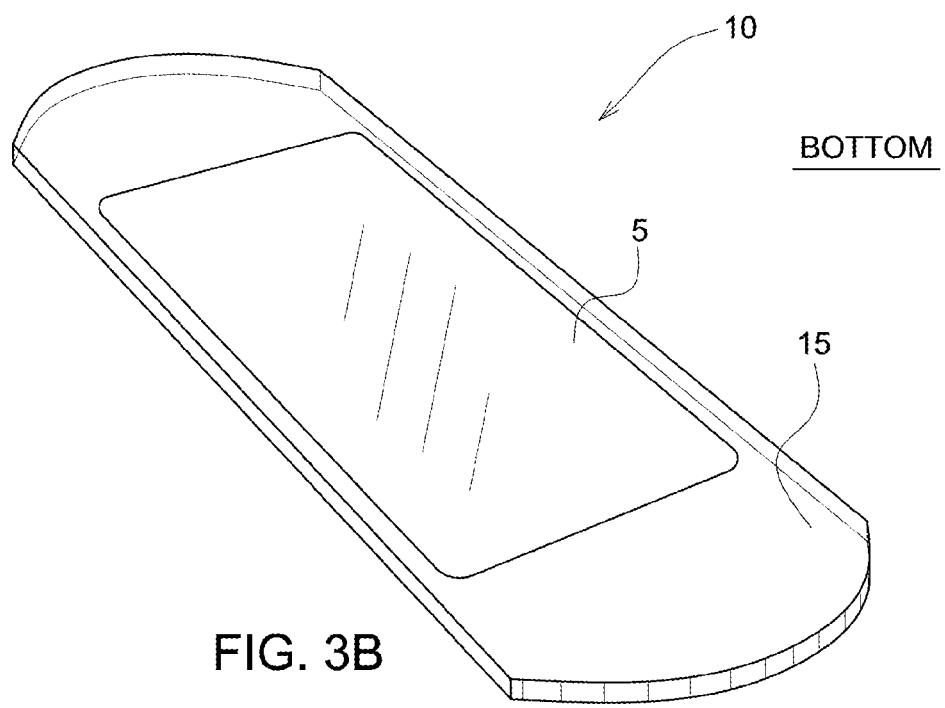
FIG. 3B depicts one embodiment of an Aluminaid™ bandage (narrow, substantially rectangular general form factor), showing the bottom-side topography that features a substantially smooth aluminum substrate, which is intended to make contact with a user's tissue.
Figure 4A:
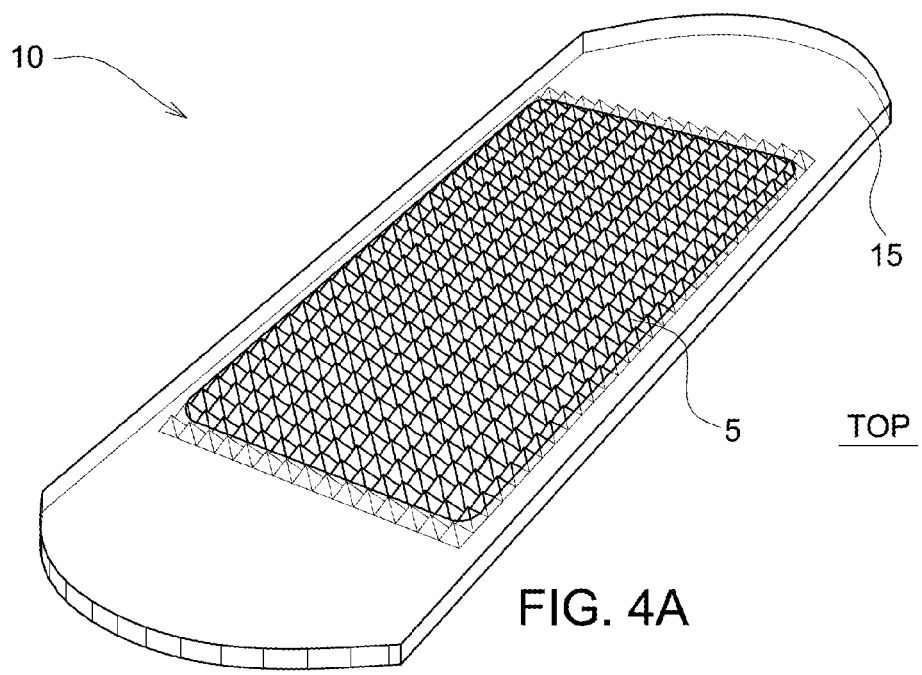
FIG. 4A depicts one embodiment of an Aluminaid™ bandage (narrow, substantially rectangular general form factor), showing the top-side topography that features a field of heat-dissipation-enhancing pyramid-like protrusions.
Figure 4B:
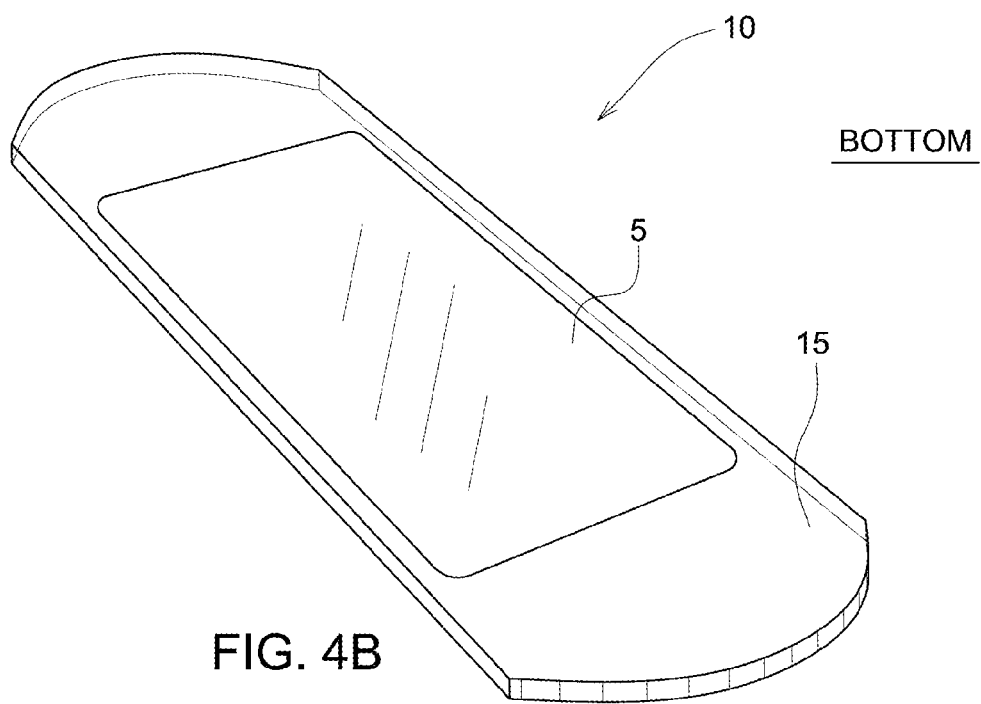
FIG. 4B depicts one embodiment of an Aluminaid™ bandage (narrow, substantially rectangular general form factor), showing the bottom-side topography that features a substantially smooth aluminum substrate, which is intended to make contact with a user's tissue.
Figure 5A:
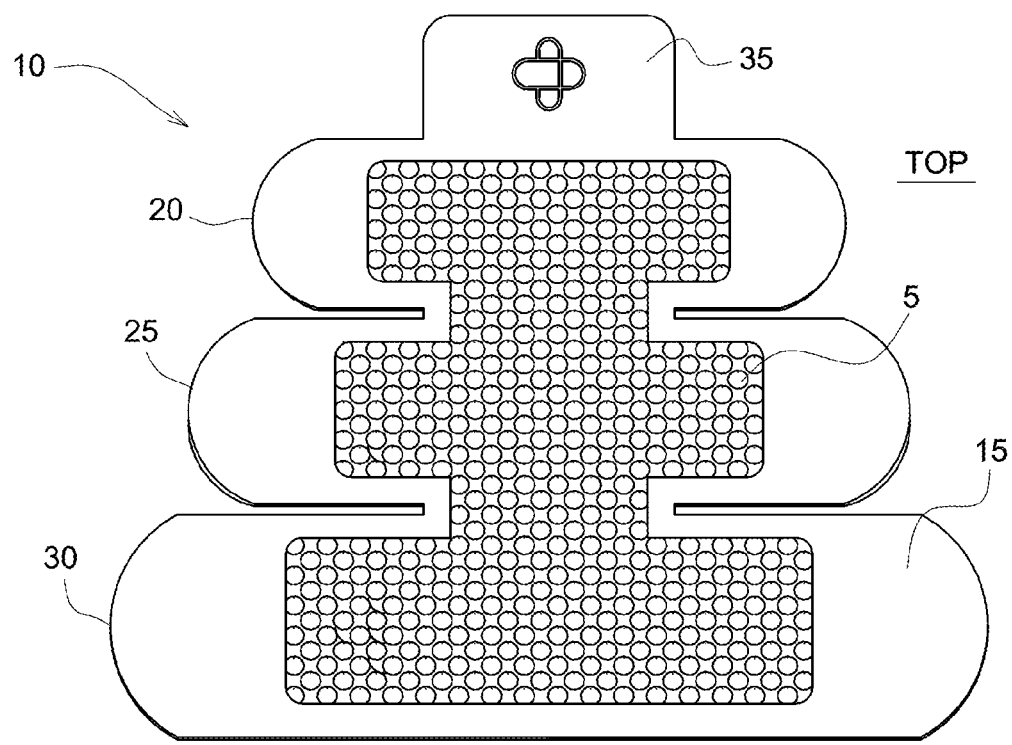
Figure 5B:
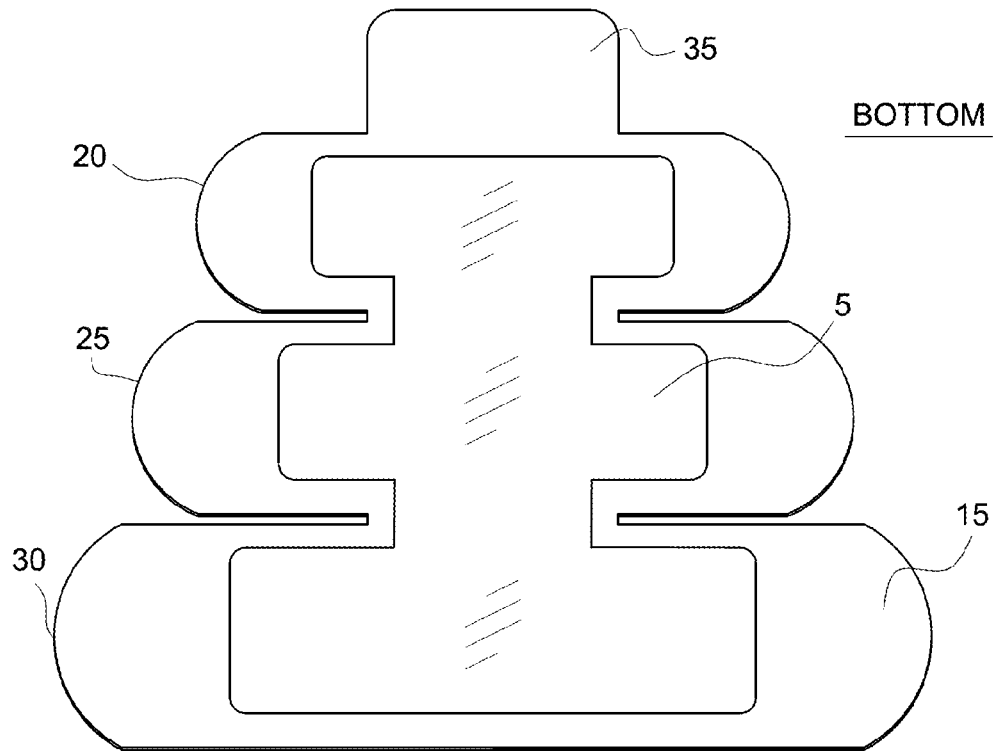
Figure 6A:
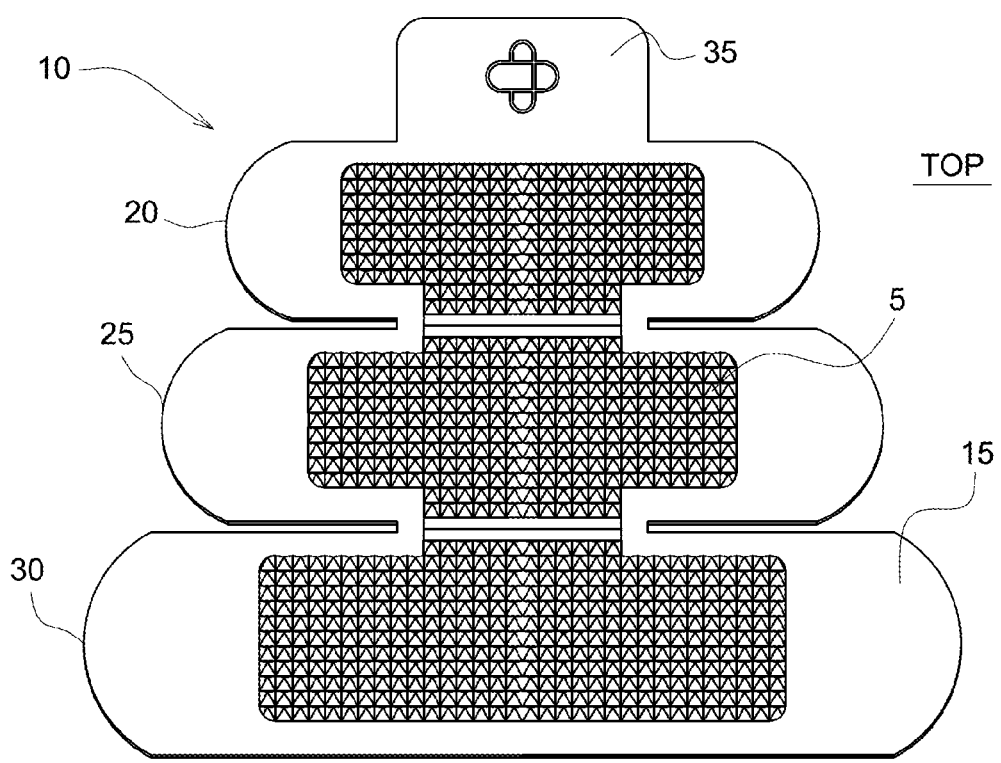
Figure 6B:
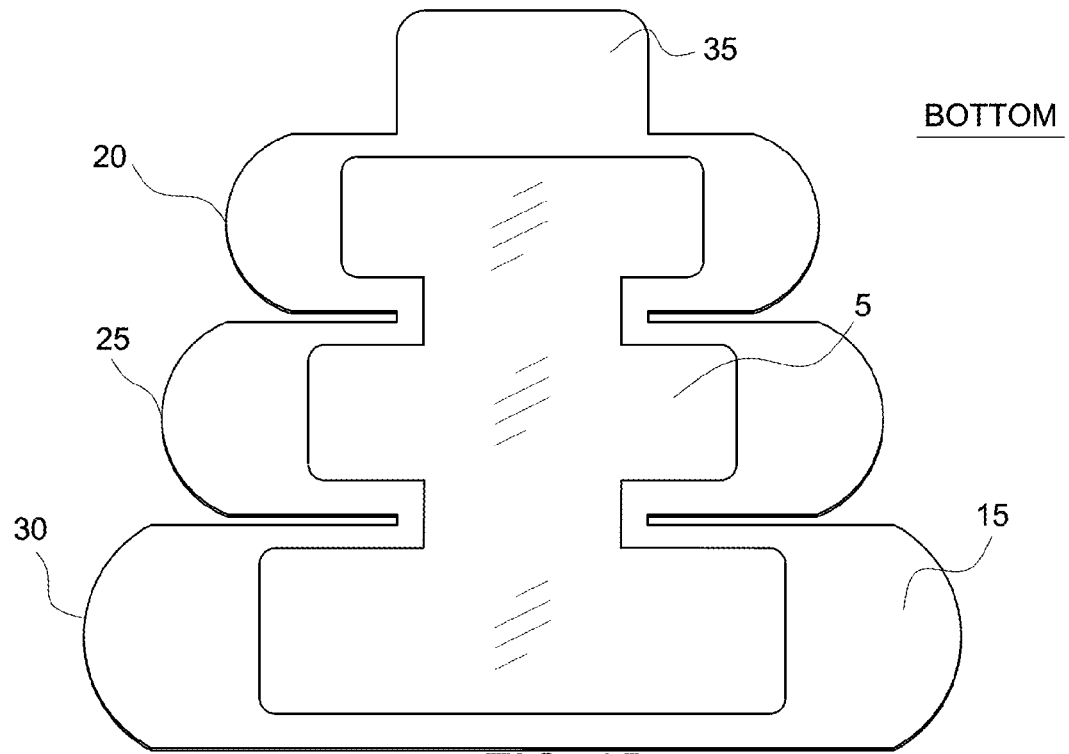
Figure 7:
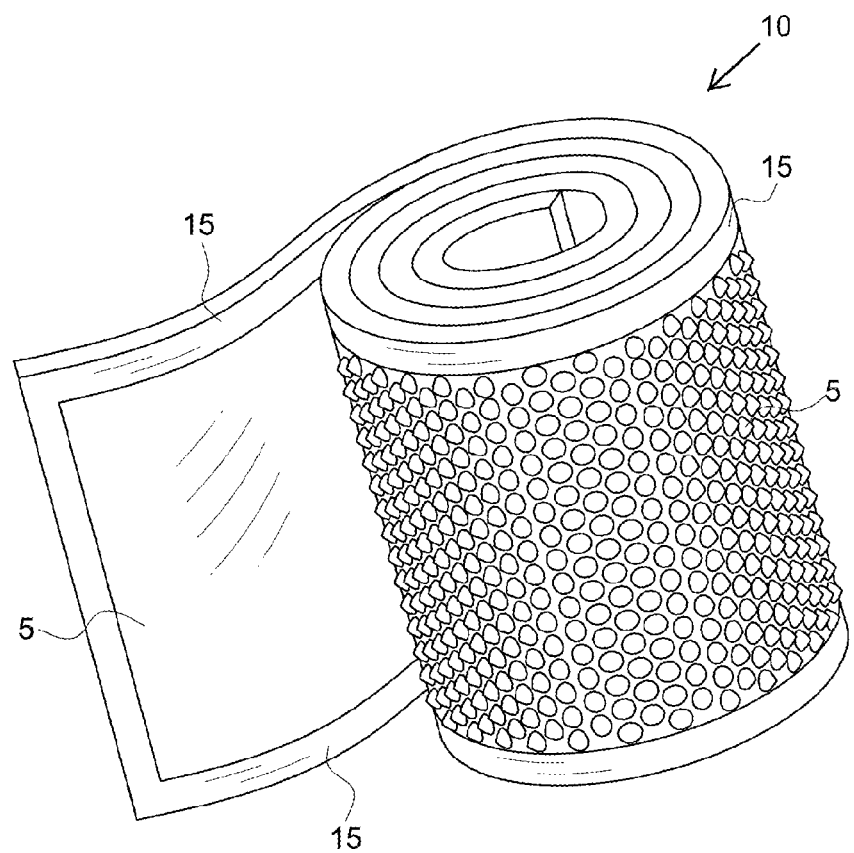
FIG. 7 depicts one embodiment of a roll of Aluminaid™ bandage material, wherein the majority of the surface area is dedicated to an aluminum substrate with a smooth side (the side to be applied to tissue) and with a side having a field of heat-dissipation-enhancing protrusions or ridges. In some embodiments, the top and bottom edges of the roll include a line of polymer material with an adhesive to facilitate attachment to a part of a user body. In other variations, these polymer-adhesive strips are not included and the dispensed amount of bandage roll is secured to a user's body with strips of medical tape and/or gauze.
Figure 8:
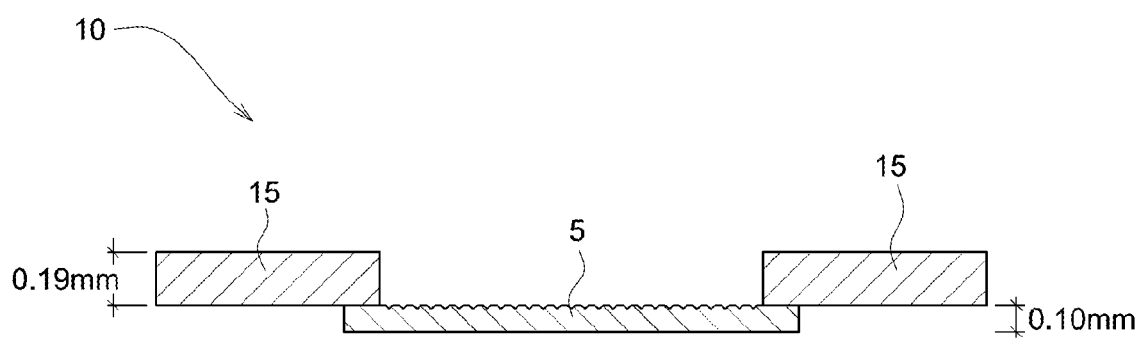
FIG. 8 depicts one embodiment of a side view of an Aluminaid™ bandage, showing the relationship between the aluminum substrate and the surrounding second layer/adhesive.
Figure 9A:
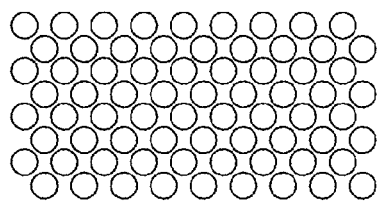
FIG. 9A depicts one embodiment of a possible topography for the air-exposed side of an Aluminaid™ bandage's aluminum substrate, featuring in this case, as an example, a plurality of rows of cone-shaped or mound-shaped protrusions, every other row staggered relative to its neighbor rows to maximize the outer surface area available to facilitate heat transfer away from a user's body/wound. In this particular example, each protrusion is shown separated by a distance along the aluminum substrate from each other, and that distance can be varied between embodiments, and can even be a zero distance in some variations).
Figure 9B:
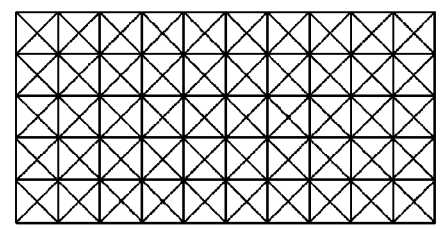
FIG. 9B depicts one embodiment of a possible topography for the air-exposed side of an Aluminaid™ bandage's aluminum substrate, featuring in this case, as an example, a plurality of rows of pyramid-shaped protrusions to maximize the outer surface area available to facilitate heat transfer away from a user's body/wound. In this particular example, each protrusion is shown immediately adjacent to each other; however, in other embodiments, the protrusions can be separated by a distance along the aluminum substrate.
Figure 10A:
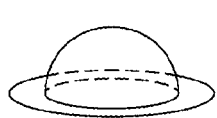
FIGS. 10A-10N each depicts one embodiment of a possible heat-dissipation-enhancing protrusions, including various exemplary embodiments of pyramid-type protrusions, cone-like protrusions, half-dome-like protrusions, and protrusions hollows manufactured in the top-center that can extend down the length of the raised protrusion and even all the way through the aluminum substrate of an Aluminaid™ bandage.
Figure 10B:
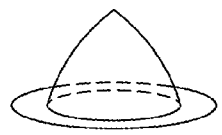
Figure 10C:
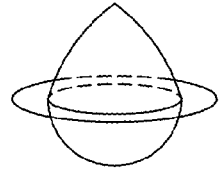
Figure 10D:
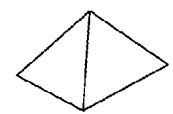
Figure 10E:
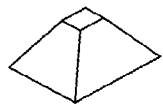
Figure 10F:
Figure 10G:
Figure 10H:
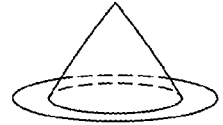
Figure 10I:
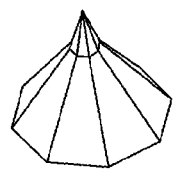
Figure 10J:
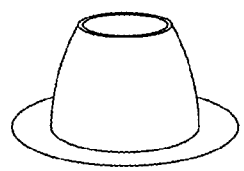
Figure 10K:
Figure 10L:
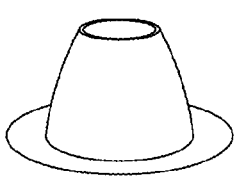
Figure 10M:
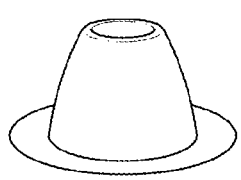
Figure 10N:
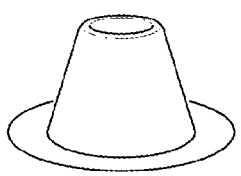
Figure 11A:
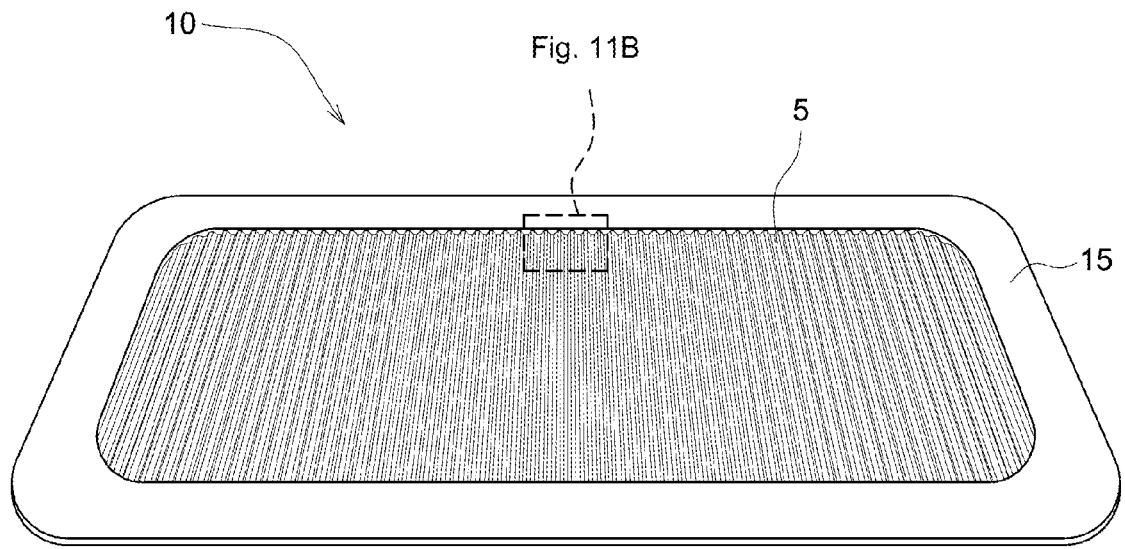
FIG. 11A depicts one embodiment of an Aluminaid™ bandage (general form factor), wherein the external surface topography of the aluminum substrate (that is, the surface not designed to be in direct contact with a user's skin) is increased with a plurality ridges in order to increase heat dissipation.
Figure 11B:
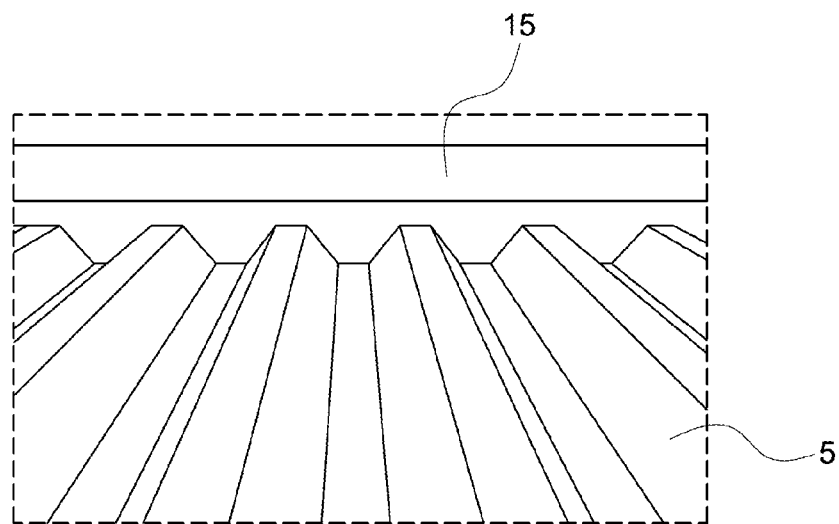
FIG. 11B depicts one embodiment of a magnified section of the aluminum substrate of the embodiment of an Aluminaid™ bandage depicted in FIG. 11A.
Figure 12A:
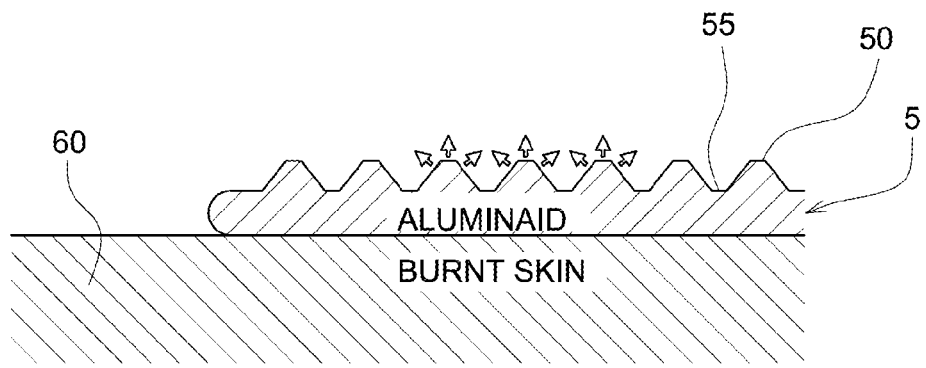
FIG. 12A depicts one embodiment of a partial-side view of an Aluminaid™ bandage (general form factor), wherein the outer surface area of the aluminum substrate (that is, the surface not designed to be in direct contact with a user's skin) is increased with a plurality of surface protrusions; e.g., ridges, cones, or pyramids; in order to increase heat dissipation.
Figure 12B:
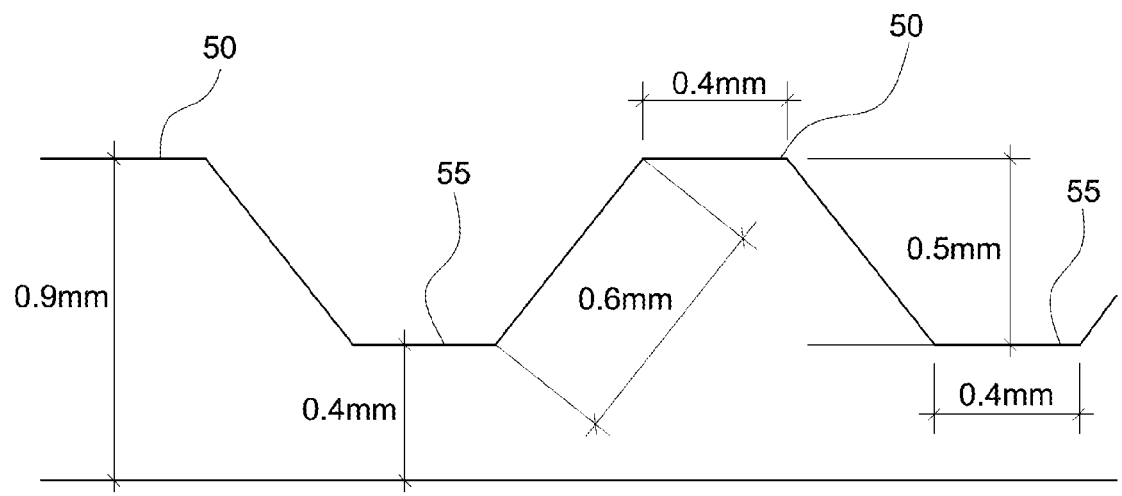
FIG. 12B depicts one embodiment of a close-up, partial side view of an Aluminaid™ bandage depicted in FIG. 12A, wherein the outer surface area of the aluminum substrate (that is, the surface not designed to be in direct contact with a user's skin) is increased with a plurality of surface protrusions; e.g., ridges, cones, or pyramids; in order to increase heat dissipation, and wherein some candidate dimensions are introduced. It should be noted that the dimensions provided are exemplary only and are not intended to limit the scope of the inventive disclosure.
Figure 13A:
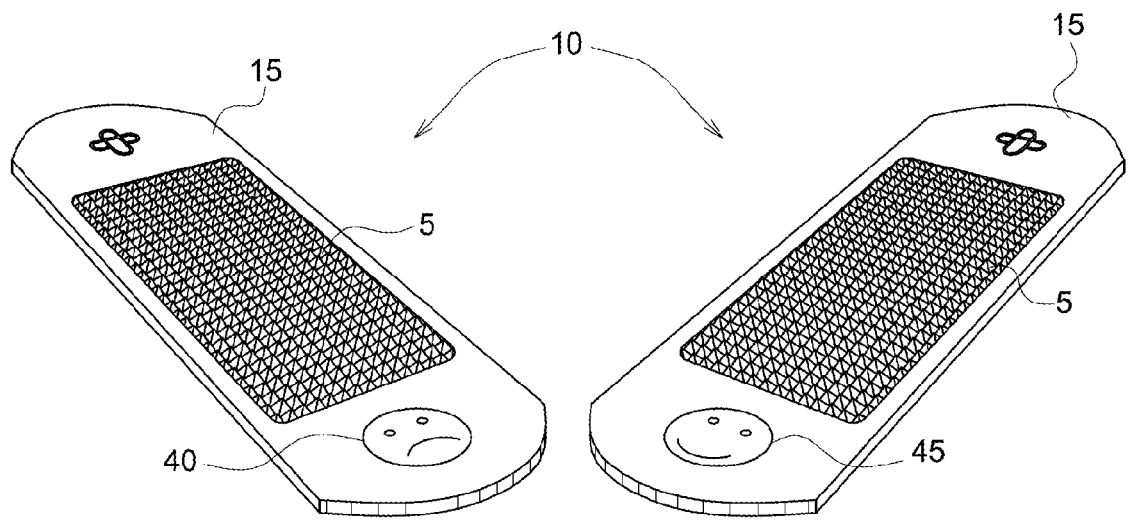
FIG. 13A depicts one embodiment of an Aluminaid™ bandage (general form factor), and also includes thermochromic visual indicators, which display themselves when the aluminum substrate to which they are coupled experiences certain temperatures.
Figure 13B:
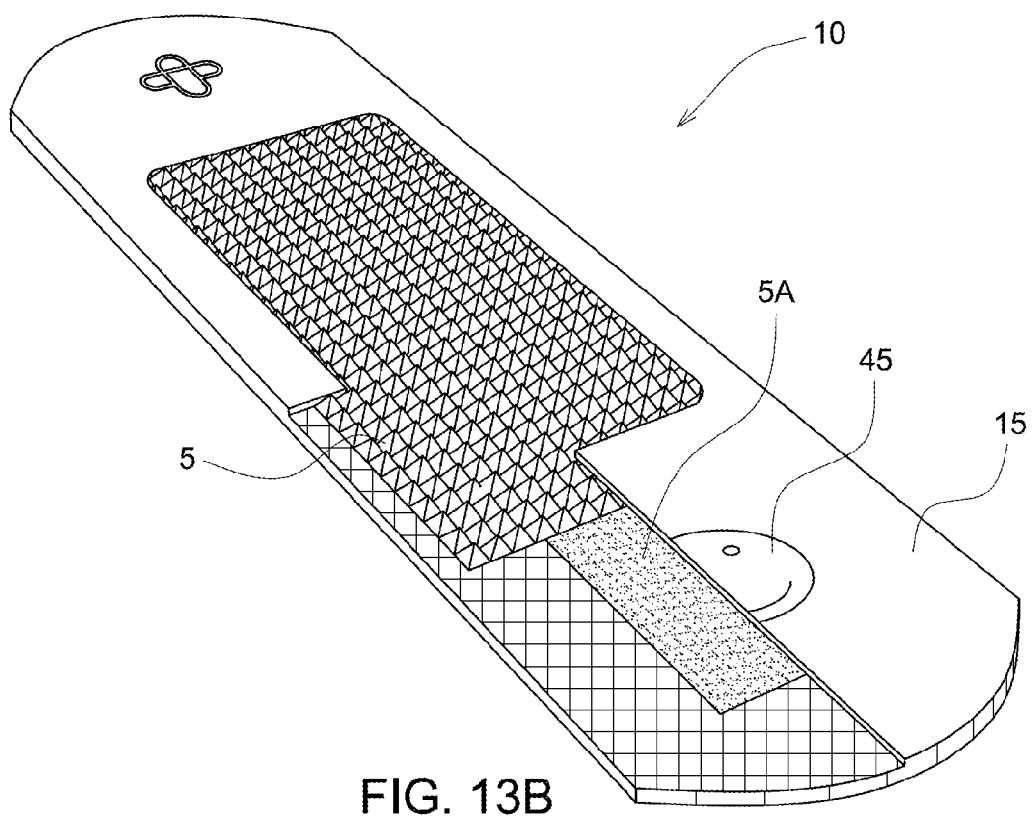
FIG. 13B depicts one embodiment of a cutaway-view of an Aluminaid™ bandage (general form factor), which also shows the relationship between the thermochromic visual indicator(s) and the aluminum substrate.
Figure 14:
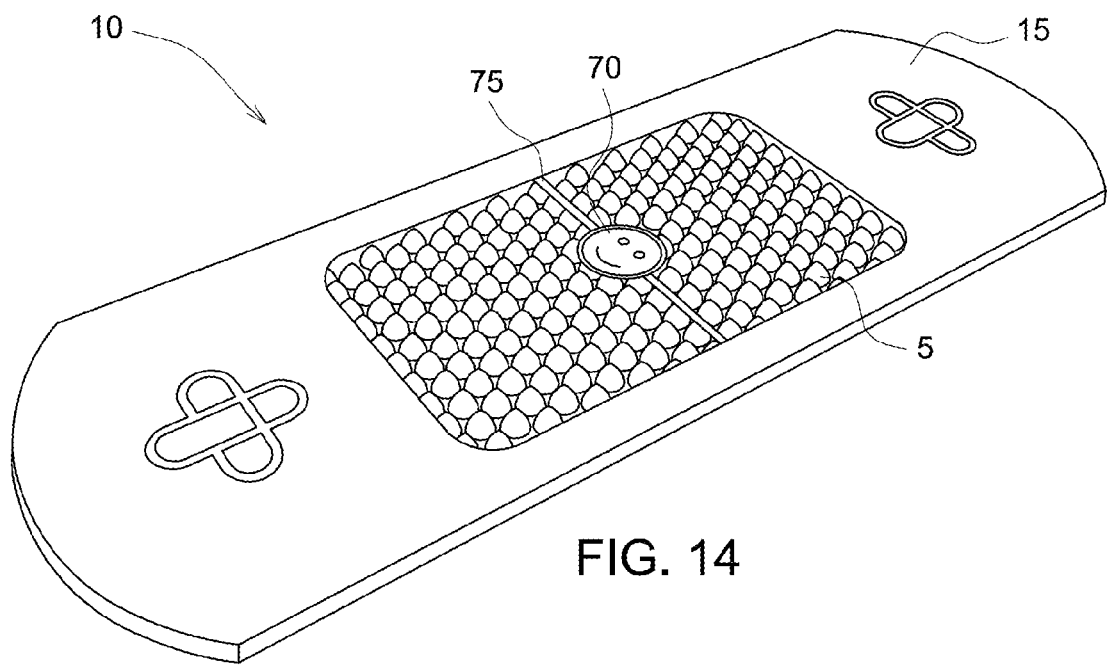
FIG. 14 depicts one embodiment of an Aluminaid™ bandage (general form factor), and also includes a thermochromic visual indicator, suspended above the aluminum substrate via a "bridge" comprised of aluminum strips, which indicates when the aluminum substrate experiences certain predetermined temperatures.
Figure 15:
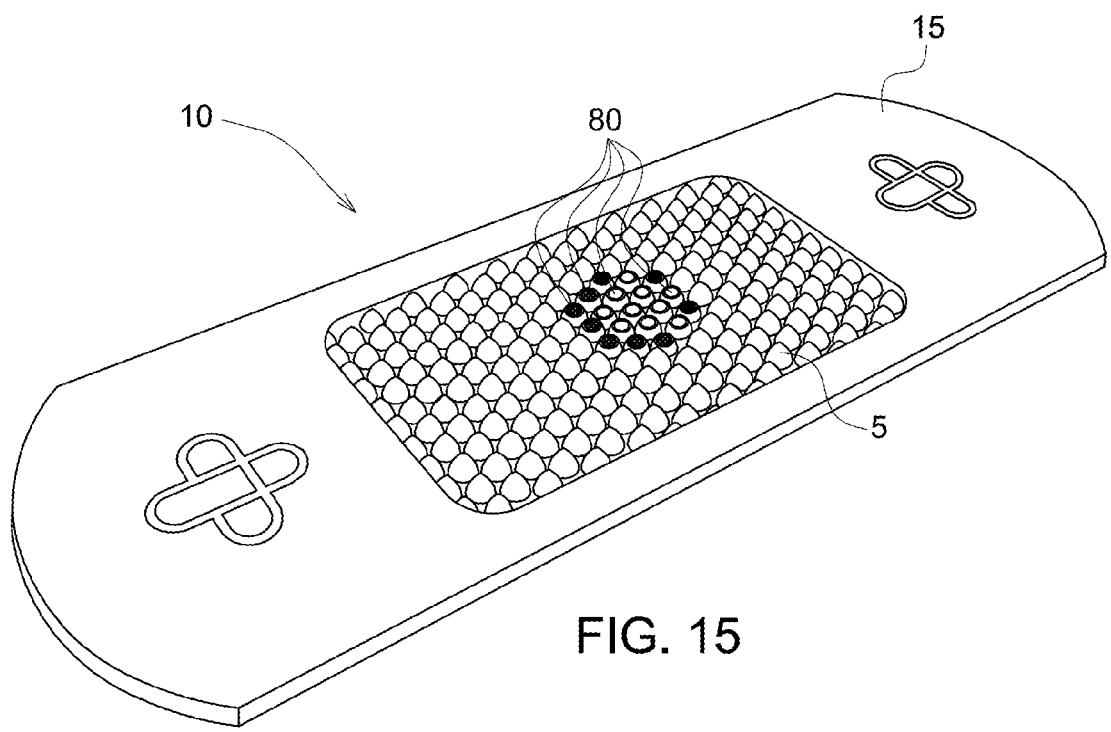
FIG. 15 depicts one embodiment of an Aluminaid™ bandage (general form factor), and also includes a thermochromic visual indicator, wherein thermochromic compound is disposed on the tops of a subset of the aluminum substrate protrusions, the subset of thermochromic coated protrusions indicating when the aluminum substrate experiences certain predetermined temperatures.
Figure 16:
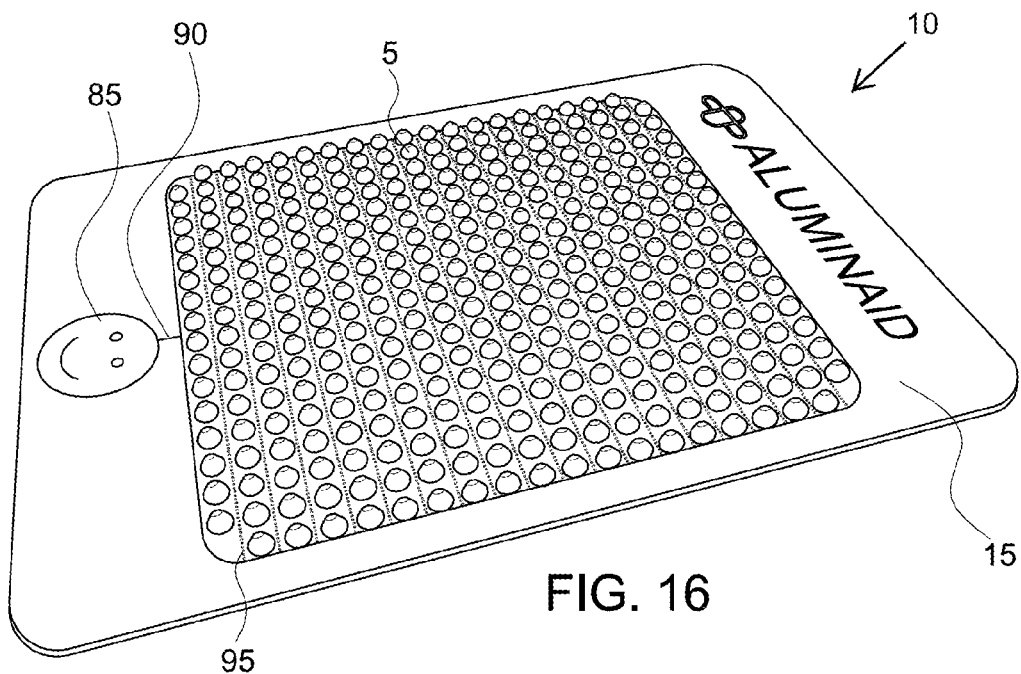
FIG. 16 depicts one embodiment of an Aluminaid™ bandage (large-rectangular general form factor), showing the top-side topography that features a field of heat-dissipation-enhancing cone-like protrusions, a thermochromic visual indicator in thermal communication with the aluminum substrate, and a plurality of rows of manufactured aeration holes to supplement the randomly occurring pinholes that are part of the normal aluminum-rolling process due to impurities. Though this particular embodiment shows only rows of aeration holes, in other variations, columns of aeration holes can be present on the aluminum substrate as well. The size and population densities of the aeration holes can be varied with particular applications.
Figure 17:
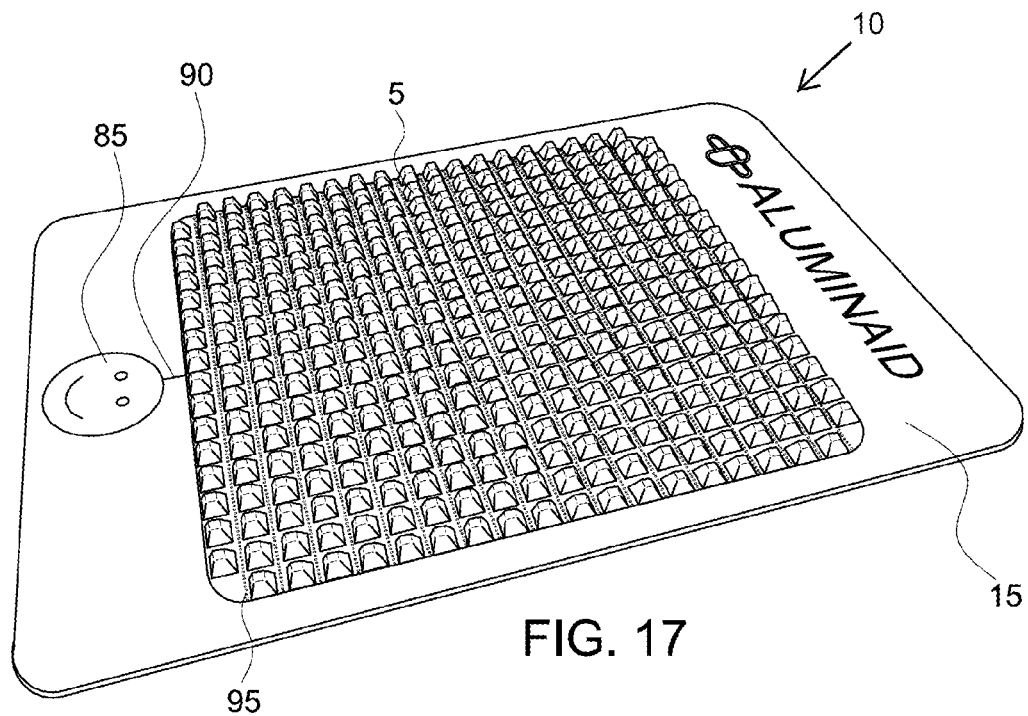
FIG. 17 depicts one embodiment of an Aluminaid™ bandage (large-rectangular general form factor), showing the top-side topography that features a field of heat-dissipation-enhancing pyramid-like protrusions, a thermochromic visual indicator in thermal communication with the aluminum substrate, and a plurality of rows of manufactured aeration holes to supplement the randomly occurring pinholes that are part of the normal aluminum-rolling process due to impurities. Though this particular embodiment shows only rows of aeration holes, in other variations, columns of aeration holes can be present on the aluminum substrate as well. The size and population densities of the aeration holes can be varied with particular applications.
Figure 18:
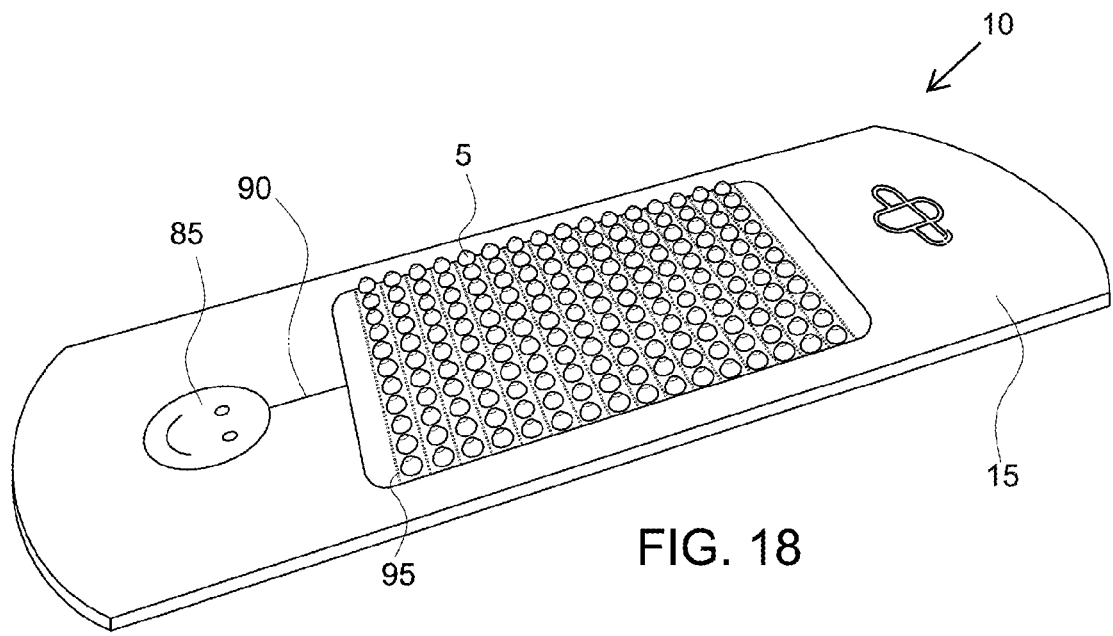
FIG. 18 depicts one embodiment of an Aluminaid™ bandage (narrow, substantially rectangular general form factor), showing the top-side topography that features a field of heat-dissipation-enhancing cone-like protrusions, a thermochromic visual indicator in thermal communication with the aluminum substrate, and a plurality of rows of manufactured aeration holes to supplement the randomly occurring pinholes that are part of the normal aluminum-rolling process due to impurities. Though this particular embodiment shows only rows of aeration holes, in other variations, columns of aeration holes can be present on the aluminum substrate as well. The size and population densities of the aeration holes can be varied with particular applications.
Figure 19:
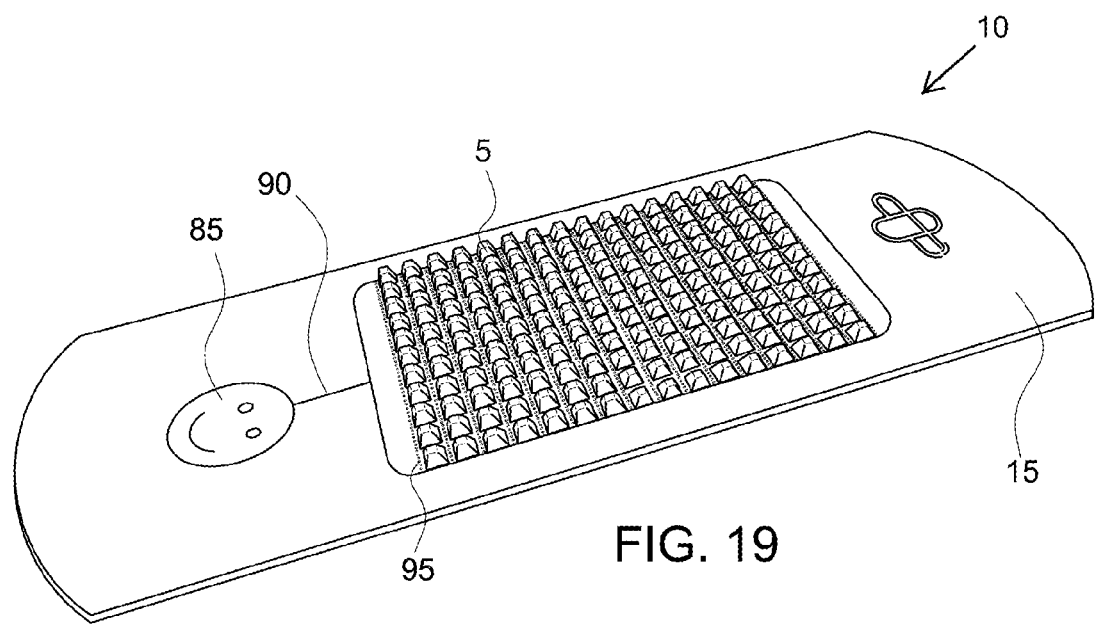
FIG. 19 depicts one embodiment of an Aluminaid™ bandage (narrow, substantially rectangular general form factor), showing the top-side topography that features a field of heat-dissipation-enhancing pyramid-like protrusions, a thermochromic visual indicator in thermal communication with the aluminum substrate, and a plurality of rows of manufactured aeration holes to supplement the randomly occurring pinholes that are part of the normal aluminum-rolling process due to impurities. Though this particular embodiment shows only rows of aeration holes, in other variations, columns of aeration holes can be present on the aluminum substrate as well. The size and population densities of the aeration holes can be varied with particular applications.
Figure 20A:
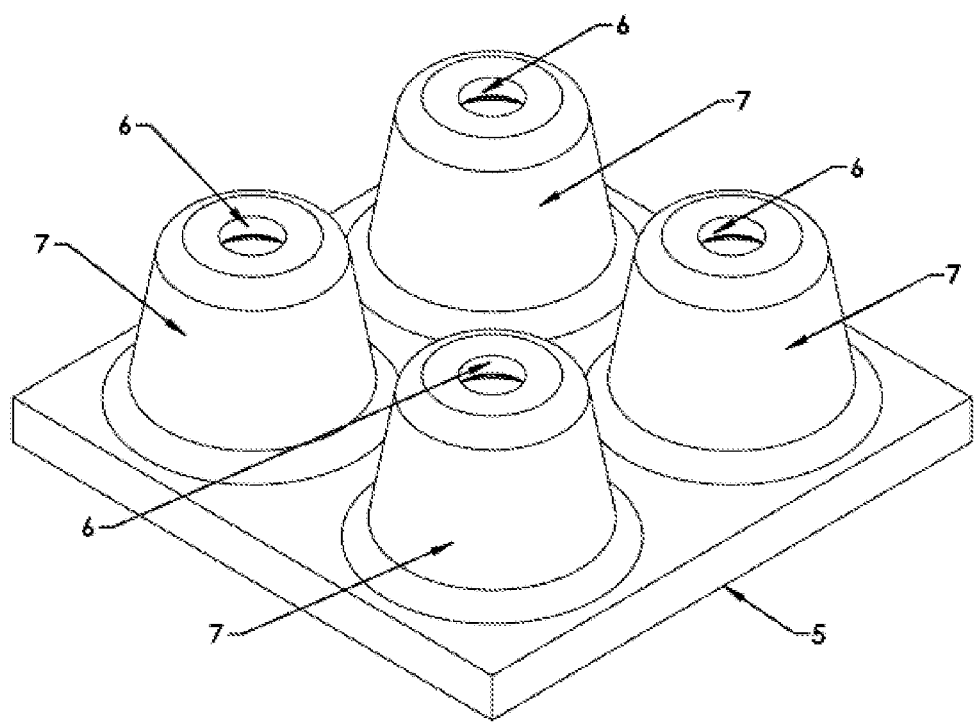
FIG. 20A depicts one embodiment of a small portion of a thermally conductive, metal-based substrate that can be used in Aluminaid™ bandage, showing a variation of the top-side topography that features a field of heat-dissipation-enhancing cone-like protrusions with holes disposed at the top of each protrusion.
Figure 20B:
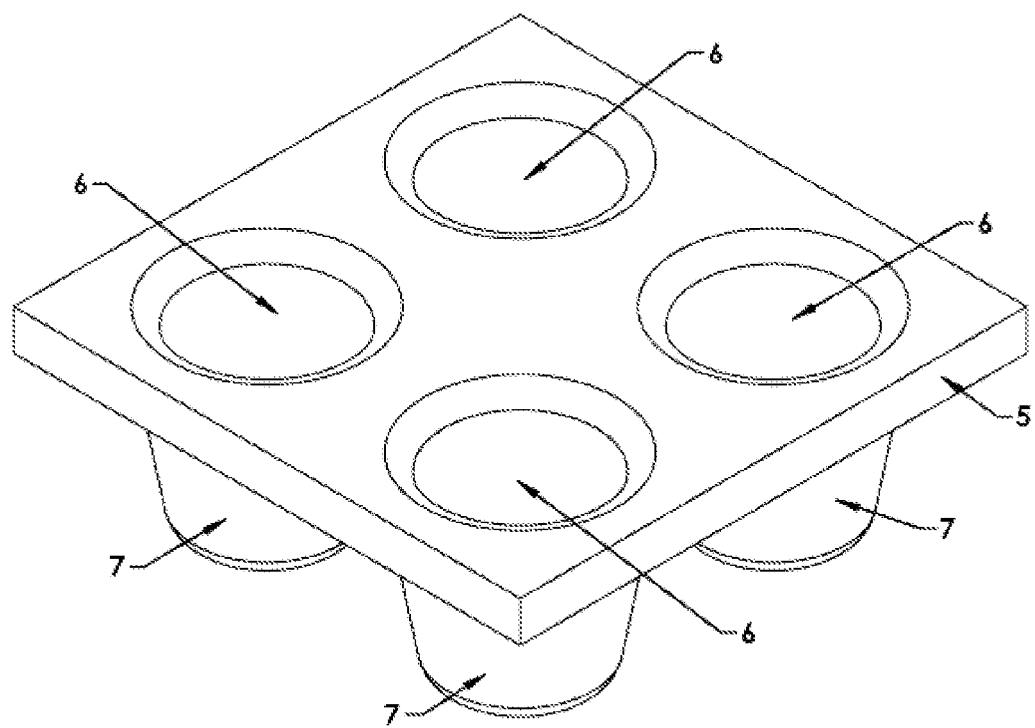
FIG. 20B depicts one embodiment of a small portion of a thermally conductive, metal-based substrate that can be used in Aluminaid™ bandage, showing a variation of the bottom-side topography that features a substantially smooth aluminum substrate interspersed with holes that extend into and through their respective heat-dissipation-enhancing cone-like protrusions. This bottom surface is adapted to make contact with a user's tissue.
Figure 21A:
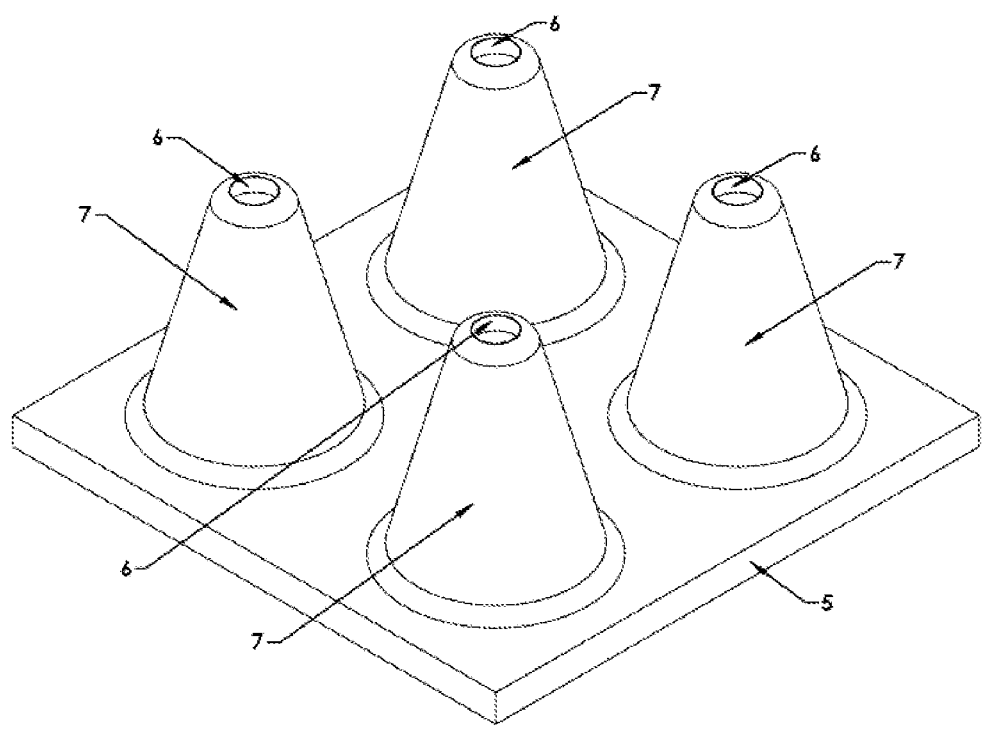
FIG. 21A depicts one embodiment of a small portion of a thermally conductive, metal-based substrate that can be used in Aluminaid™ bandage, showing a variation of the top-side topography that features a field of heat-dissipation-enhancing cone-like protrusions with holes disposed at the top of each protrusion.
Figure 21B:
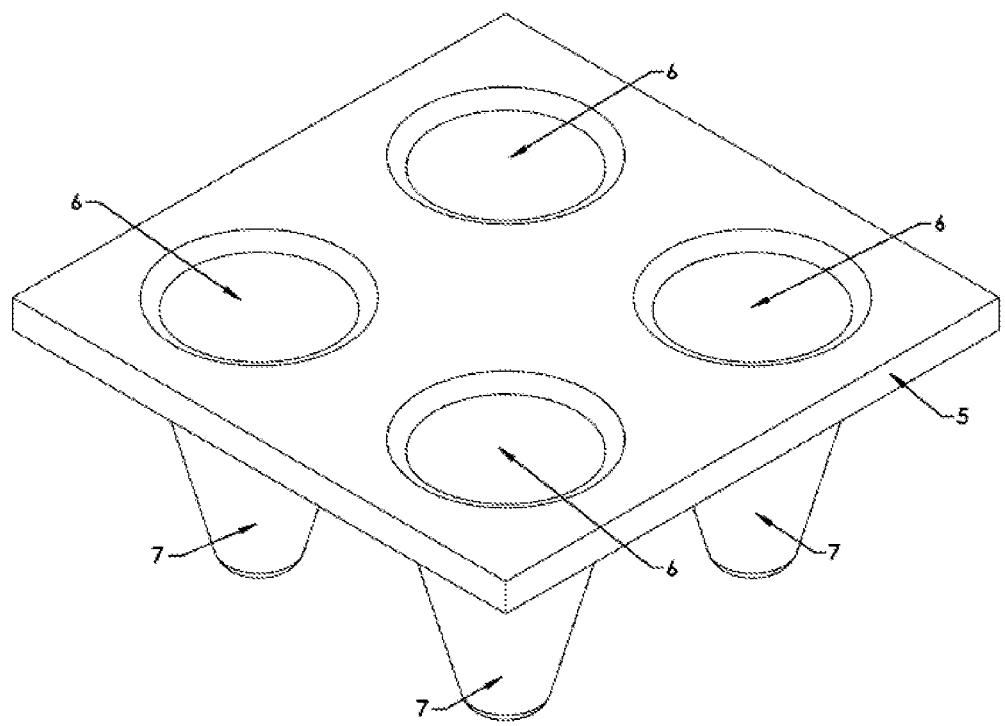
FIG. 21B depicts one embodiment of a small portion of a thermally conductive, metal-based substrate that can be used in Aluminaid™ bandage, showing a variation of the bottom-side topography that features a substantially smooth aluminum substrate interspersed with holes that extend into and through their respective heat-dissipation-enhancing cone-like protrusions. This bottom surface is adapted to make contact with a user's tissue.
Figure 22A:
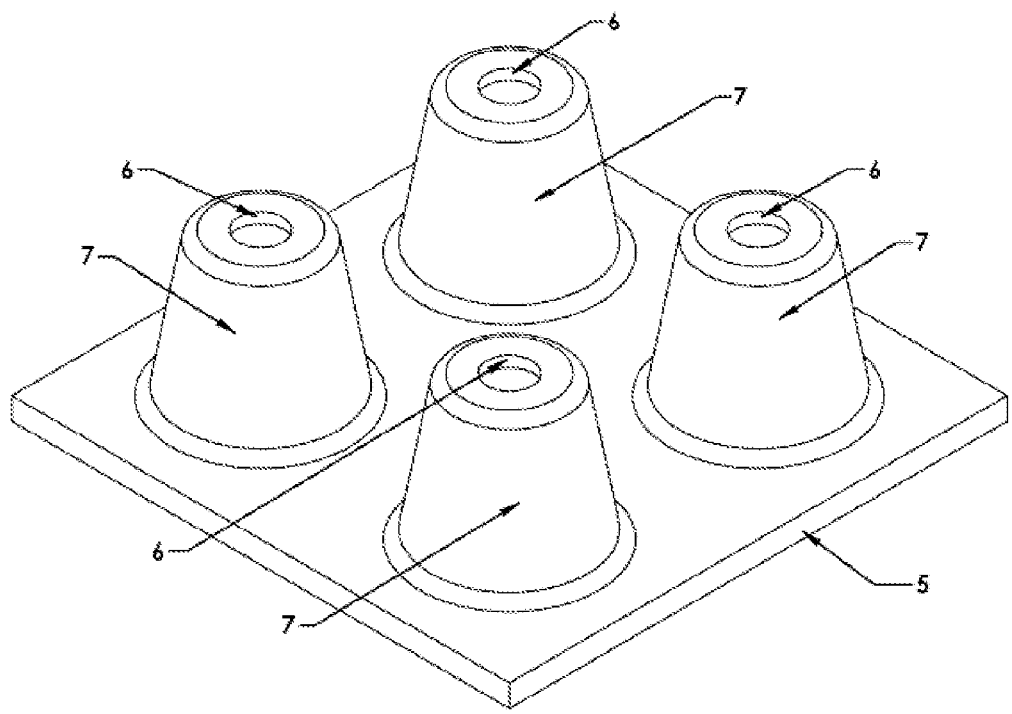
FIG. 22A depicts one embodiment of a small portion of a thermally conductive, metal-based substrate that can be used in Aluminaid™ bandage, showing a variation of the top-side topography that features a field of heat-dissipation-enhancing cone-like protrusions with holes disposed at the top of each protrusion.
Figure 22B:
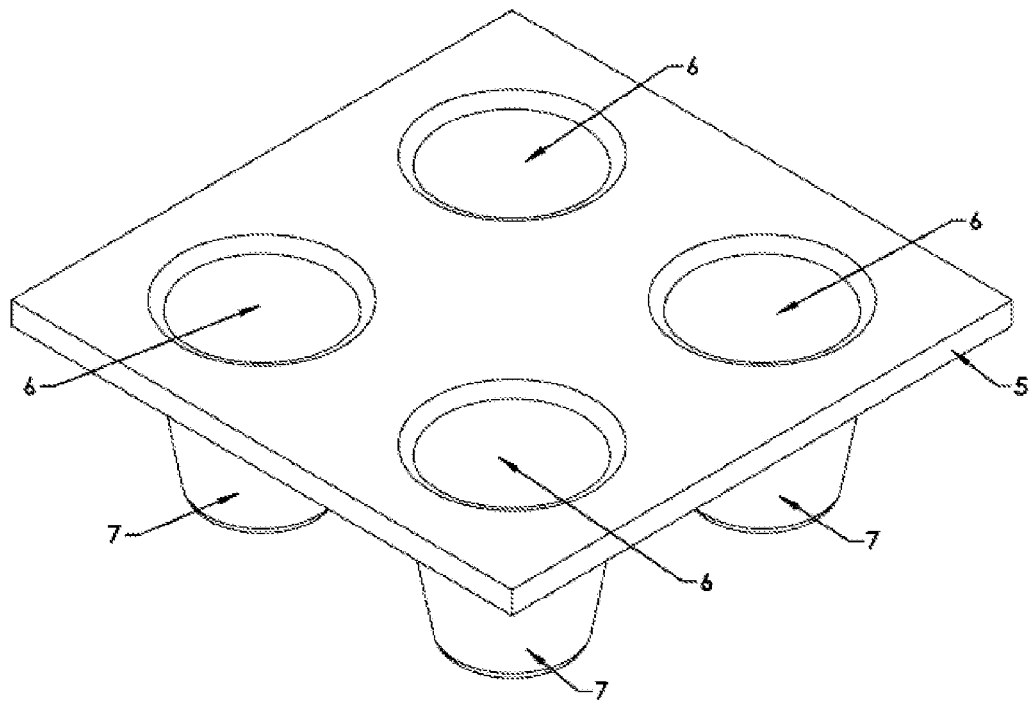
FIG. 22B depicts one embodiment of a small portion of a thermally conductive, metal-based substrate that can be used in Aluminaid™ bandage, showing a variation of the bottom-side topography that features a substantially smooth aluminum substrate interspersed with holes that extend into and through their respective heat-dissipation-enhancing cone-like protrusions. This bottom surface is adapted to make contact with a user's tissue.
Figure 23A:
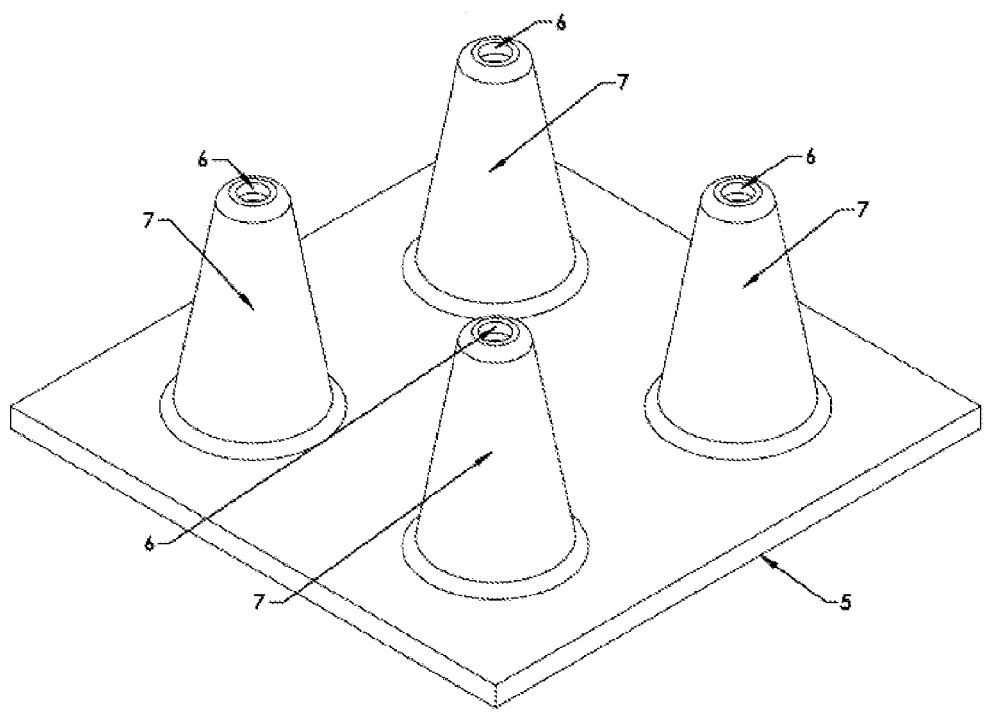
FIG. 23A depicts one embodiment of a small portion of a thermally conductive, metal-based substrate that can be used in Aluminaid™ bandage, showing a variation of the top-side topography that features a field of heat-dissipation-enhancing cone-like protrusions with holes disposed at the top of each protrusion.
Figure 23B:
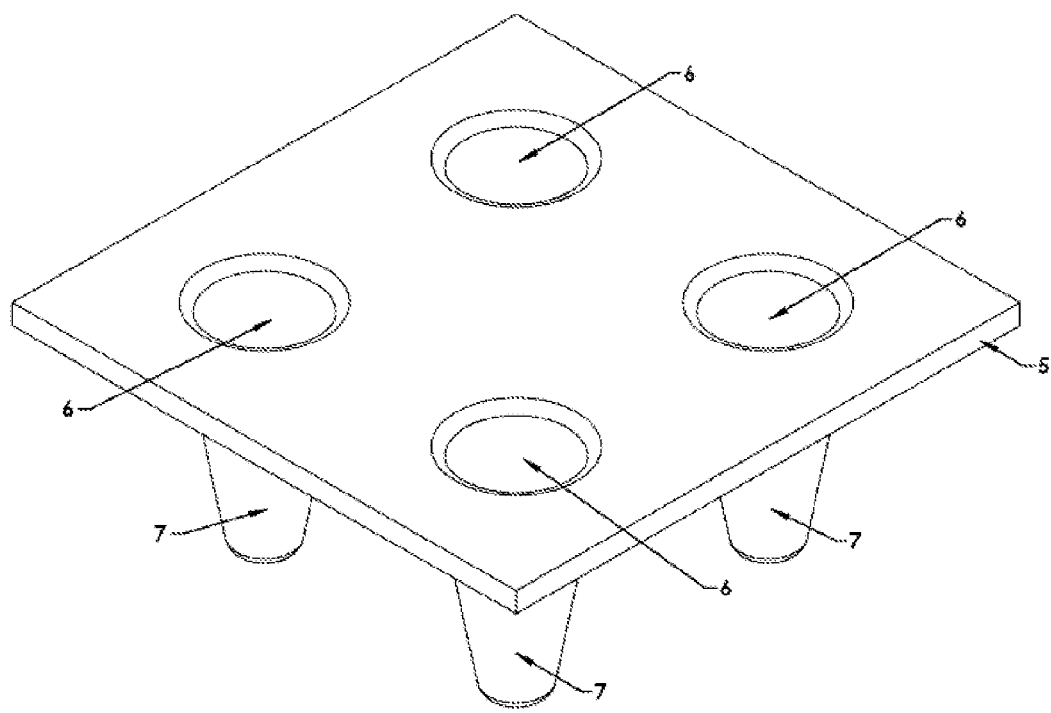
FIG. 23B depicts one embodiment of a small portion of a thermally conductive, metal-based substrate that can be used in Aluminaid™ bandage, showing a variation of the bottom-side topography that features a substantially smooth aluminum substrate interspersed with holes that extend into and through their respective heat-dissipation-enhancing cone-like protrusions. This bottom surface is adapted to make contact with a user's tissue.

The inventive disclosure contained herein is generally directed to a class of medical products that in many embodiments are effective in the treatment of tissue burns, whether be burns due to thermal burns, sun exposure, or rashes. Included in such products are various specialized bandages and wraps that incorporate an extremely thin layer of thermally conductive metal with uniquely enhanced material and surface features to ensure flexibility and effective heat-transfer characteristics to cool a burn wound.

Aluminum is generally favored as the basis of the bandages because besides exhibiting multiple properties that are beneficial to healing certain types of tissue wounds, as discussed infra, aluminum is non-toxic, easy to sterilize, relatively inexpensive and easy to fabricate with, and abundantly mined worldwide. Hereinafter, the overall class of products described in this patent application is referred to as "Aluminaid™" or "Aluminaids™"

II. Terminology

The terms and phrases as indicated in quotes (" ") in this section are intended to have the meaning ascribed to them in this Terminology section applied to them throughout this patent application, unless clearly indicated otherwise in context. Further, as applicable, the stated definitions are to apply, regardless of the word or phrase's case, to the singular and plural variations of the defined word or phrase.

The term "or", as used in this patent application, is not meant to be exclusive; rather, the term is inclusive, meaning "either or both".

References in this patent application to "one embodiment", "an embodiment", "a preferred embodiment", "an alternative embodiment", "a variation", "one variation", and similar phrases mean that a particular feature, structure, or characteristic described in connection with the embodiment is included in at least an embodiment of the invention. The appearances of the phrase "in one embodiment" and/or "in one variation" in various places in this patent application are not necessarily all meant to refer to the same embodiment.

The term "couple" or "coupled", as used in this specification and the appended claims, refers to either an indirect or a direct connection between the identified elements, components, or objects. Often, the manner of the coupling will be related specifically to the manner in which the two coupled elements interact.

The terms "removable", "removably coupled", "readily removable", "readily detachable", "detachably coupled", and similar terms, as used in this patent application specification (including the claims and drawings), refer to structures that can be uncoupled from an adjoining structure with relative ease (i.e., non-destructively, and without a complicated or time-consuming process) and that can also be readily reattached or coupled to the previously adjoining structure.

The term "bonded", "bonding", and similar terms, as used in this patent application specification (including the claims and drawings), refer to any means that is used to fixedly couple two or more structures together, such as the layers in the construction of some embodiments of Aluminaid™ bandages. Examples of bonding include the use of adhesives between surfaces, ultrasonic welding, thermoplastic welding, etc.

Directional and/or relational terms such as, but not limited to, left, right, nadir, apex, top, bottom, vertical, horizontal, back, front, and lateral are relative to each other, are dependent on the specific orientation of an applicable element or article, are used accordingly to aid in the description of the various embodiments in this specification and the appended claims, and are not necessarily intended to be construed as limiting.

As applicable, the terms "about" or "generally", as used herein in the specification and appended claims, and unless otherwise indicated, means a margin of +−20%. Also, as applicable, the term "substantially" as used herein in the specification and appended claims, unless otherwise indicated, means a margin of +−10%. It is to be appreciated that not all uses of the above terms are quantifiable such that the referenced ranges can be applied.

The term "aluminum", "aluminum compound", aluminum alloy", and similar terms, as used in this patent application (including the drawings and claims), refer to any material is substantially comprised of the element Aluminum (Period Element Symbol "Al", atomic number 13). Generally, any machined or otherwise processed aluminum composition or structure (e.g., very thin aluminum sheets or strips) that can be effectively incorporated into a medicinal ointment or cream, or into sheeting to make special bandages, is included in this definition. Examples of aluminum-based molecular compounds that can be used with the teachings of this disclosure include aluminum oxides (e.g. $Al_2O_3$), aluminum sulfates (e.g., $Al_2(SO_4)_3(H_2O)_{18}$), aluminum chlorides (e.g., $AlCl_3$), aluminum salts (e.g., aluminum diacetate (HOAl$(C_2H_3O_2)_2$)), etc. Many such compounds can be used by the teachings of this disclosure to enhance the effectiveness of aluminum-based or aluminum-infused medical and first-aid products. For example, aluminum diacetate can enhance the antiseptic and astringent properties of a medical bandage, while also enhancing the thermal conductivity away from a burn wound.

III. Aluminaid™ Bandages and/or Wraps

A. Aluminaid™ Theory of Operation

Aluminaid™ products deploy natural occurrences of physics combined with specific application and form factor. Essentially, Aluminaids™ include the physical properties inherent in aluminum, such as "specific heat capacity" and "thermal conductivity".

Taking an Aluminaid™ bandage as an example, specific heat capacity accounts for the amount of heat that the aluminum foil disposed in the bandage can store at any one time and thermal conductivity accounts for how fast that aluminum material can potentially conduct heat (somewhat analogous to how fast an electrical wire of a given material can conduct electricity).

There are three ways in which thermal energy transfer can be described:

Conduction;

Convection; and

Radiation.

Conduction requires physical contact (similar to the flow of electricity in wire). Convection emanates from the movement of molecules (e.g., the way in which heated and cooled water or other fluid moves up and down). Radiation does not necessarily involve direct contact (e.g., the way the sun emits light rays).

At any given temperature, a given mass of aluminum holds much less energy than an equivalent mass of human flesh. For instance, in convection or conduction, if one touches aluminum foil from an oven during the cooking process, a subject's hand and the foil share the thermal energy. The hand (of much greater mass) requires much more energy to raise its temperature (if at all, depending upon the physical connection between the foil and the food). When the subject touches aluminum foil, the foil transfers heat to the flesh; however, due to the aluminum's low specific-heat capacity, the foil quickly loses energy, barely raising the temperature of the skin in contact. Because aluminum foil does not effectively store conducted heat, it therefore facilitates the "cooling" of a burn whilst simultaneously (in part) preventing other associated risks such as infection, dehydration, and hypothermic symptoms.

While aluminum does not effectively store conducted heat, aluminum is nonetheless an excellent conductor of heat. Aluminum will conduct any heat from the point of contact and will readily give the heat up to any heat sink, even to the ambient. This has a cooling effect to the source of the thermal heat and a heating effect to the heat sink.

In short, aluminum foil can be an effective conductor of a subject's body heat, alleviating pain which emanates from added warmth on a subject's burn wound.

Table 1 shows the comparatively low specific resistance of aluminum:

TABLE 1

Comparison of Specific Resistance of Aluminum to Various Metals at 20 Degrees Celsius

| Material Element/Alloy | ohm-cmil/ft. | micro-ohm-cm |
|---|---|---|
| Platinum (Element) | 63.16 | 10.5 |
| Tungsten (Element) | 31.76 | 5.28 |
| Magnesium (Element) | 26.41 | 4.390 |
| Aluminum (Element) | 15.94 | 2.650 |
| Gold (Element) | 13.32 | 2.214 |
| Copper (Element) | 10.09 | 1.678 |
| Silver (Element) | 9.546 | 1.587 |

Of course, there are other metals with thermal-conductivity characteristics that are equal to or better than that of aluminum. However, bandage dressings based on such alternative metals; e.g., platinum or tungsten; are generally significantly more expensive to use and/or are not as easy to work with in the manufacturing process when compared to aluminum and various aluminum alloys. Nevertheless, though aluminum is a preferred material when taking into account its cost, thermal conductivity, and other physical properties that make manufacturing easier, it should be appreciated by those skilled in the art that the special heat-dissipation-enhancing configurations for bandage metal substrates disclosed herein can also be applied to substrates made of metals other than aluminum.

Further still, aluminum foil as a dry, sterile, initial covering for thermal burns under occlusive pressure dressings has been presented as a method of diminishing the maceration of a burn surface. The method appears to influence favorably the local result by elimination of the use of ointments, and by facilitating the dispersion of exudate to the periphery of the burn. No evidence of toxicity as a result of the treatment was found. The systemic reaction was, if anything, less obvious.

This elimination or at least minimization of applied ointments and other topical treatments by employing aluminum-based bandages and/or wrapping can help avoid adverse consequences to a patient. For example, titanium dioxide exposure cream, as a burn ointment, was considered to be irritating from the evidence of production of pain, delayed healing, and possible destruction of epithelial remnants. Moreover, it has been observed that when massive doses of ascorbic acid was administered to burn patients, the doses quickly corrected the state of ascorbic acid depletion; however, the general systemic reaction to thermal burns was not found to be influenced by this form of treatment, and the general signs of illness were marked in severe cases.

B. General Aluminaid™ Bandage Forms

Refer to FIGS. 1A-31G (in particular, FIGS. 20A-31G depict some preferred designs), which depict examples of some exemplary embodiments of Aluminaid™ bandages, which are discussed in the written disclosure herein. It should be noted that many of the exemplary embodiments have similar, but differently configured components, and as such said components are given common reference numbers. For example, all embodiments of the Aluminaid™ bandages include an aluminum substrate, given the reference number of "5", and the bandage in general is assigned the reference number of "10". If an embodiment is so equipped, the surrounding outer second-layer substrate is assigned the reference number of "15". In some embodiments, an intermediate surrounding absorbent layer is disposed between the perimeter of the aluminum substrate 5 and the outer second layer 15, and this intermediate layer is assigned the reference number of "12". In still other variations, a transfer adhesive layer is disposed between the perimeter of the aluminum substrate 5 and the perimeter of the absorbent layer 12, and this transfer adhesive layer is assigned the reference number of "13". Finally, in many embodiments, an easily removable bandage-backing layer is disposed across the entire bottom surface of a bandage 10, and this back layer is assigned the reference number of "14". However, if a given discussion of a bandage component is particularly tied to a specific Figure, then the Figure number is provided along with the reference number.

In many embodiments, Aluminaid™ bandages 10 are designed for use in the treatment of low-degrees of burn instances (usually first or second-degree burns). In specific embodiments directed to bandages and other types of applied medical wrappings, Aluminaid™ bandages 10 are designed to fit most body shapes, sizes, and provision for children, teenagers, and adults (of both genders). In typical embodiments, the aluminum base 5 of a bandage 10 is coupled about its perimeter with a material 15 to facilitate adhesive coupling to user skin, wherein the second material 15 extends beyond the boundaries of the aluminum substrate 5. In some variations, the aluminum base 5 of a bandage 10 is coupled about its perimeter to the outer second material 15 via an intermediate absorbent layer 12, wherein the absorbent layer 12 can be any appropriate sterile and absorbent material, such as gauze, but is preferably made of hydrogel.

In other variations, the aluminum base 5 has a smooth side adapted to make direct contact with a burn wound, while the other side is manufactured to have a plurality of heat-dissipation-enhancing surface protrusions; such as cone, half-sphere, or pyramid shaped-shaped nodes (see, e.g., FIGS. 10A-10N and 20A-24B). In still another variation, the aluminum base 5 is substantially manufactured by a stamping process wherein a plurality of said heat-dissipation-enhancing surface protrusions are present on one side (and are substantially hollowed-out from the stamping process) while the other side, adapted to make contact with tissue, presents a plurality of voids/holes as a result of the manufacturing process. In this variation, said voids/holes aid in aeration of wounds and this type of topography is especially effective for enhancing thermal convection processes for cooling wounds.

In many embodiments, each Aluminaid™ product can be designed to fit a wide variety of different form factors directly relating to specific body parts, such as fingers and hands. For example, a wrap-around bandage adapted to create a form-fitting mitt with a thin aluminum lining to thermally conduct heat away from the burned tissue of a hand can be used, wherein the outer surface of the mitt exposes the other side of the aluminum lining to the air for heat dissipation. In other variations, more-general form factors; such as circular, rectangular strips, ovals, etc. are used to produce general-purposes pads. (See, e.g., FIGS. 1A-7; 11A-11B; and 31A-31G.) Such embodiments are adapted to easily conform to the contours of specific parts of the body, but are sufficiently robust to avoid fractionation specifically during application, thus aiding healing and subsequent bandage removal.

In still other embodiments, aluminum foils 5 up to 0.5 mil thick are used, which are impermeable to oxygen and water, and which become slightly permeable due to minute pinholes caused by the production process. In other variations, however, such permeability can be desirable in cases where a medical professional desires to allow a burn wound to drain and dry out, while still providing the thermal-conduction benefits of the applied aluminum.

It should be noted that due to the manufacturing process, typical aluminum foil has a shiny side and a matte side (the reflectivity of the shiny side is typically 88%, while the dull, matte side typically has about 80% reflectivity). However, there does not appear to be any statistically significant difference in effectiveness between applications where the shiny side is applied to the wound or where the matte side is applied to the wound 60. The shiny side is produced when the aluminum is rolled during the final pass. It is difficult to produce rollers with a gap fine enough to cope with the foil gauge; therefore, for the final pass, two sheets are rolled at the same time, doubling the thickness of the gauge at entry to the rollers. When the sheets are later separated, the inside surface is dull, and the outside surface is shiny. The resultant manufactured material is often gas and liquid permeable. In some other embodiments, the aluminum substrate 5 of the bandage is comprised of either permeable aluminum foils or sheets/strips of aluminum foils with intentionally manufactured gaps.

In order to enhance the heat-dissipation capabilities and efficacy of Aluminaid™ bandages 10, the mass of the aluminum substrate 5 is strategically configured via top-side topographies that both optimize the overall mass of the aluminum substrate enough to improve thermal conductivity at the bio-interface of the bandage 10, as well as increase the available exposed surface area in order to increase thermal convection processes to the ambient air. The thermal-conduction processes are important during the immediate period of a few seconds to a minute after bandage application to a burn wound; however, thereafter, the thermal-convection processes are considered more significant to continued wound cooling. Therefore, in the long run, it has been found that wound-cooling efficacy is improved by ensuring that the formation and topography of the aluminum substrate 5 is such that thermal-convection processes are optimized.

In still more embodiments, the aluminum substrate 5 is manufactured for one side to include a plurality of very small protrusions and/or corrugations, which increases the effective surface area for the dissipation of heat away from a burn wound. For example, referring to FIGS. 1A-7 and 20A-30, in a variation, the outer surface area of the aluminum substrate 5 (that is, the surface not designed to be in direct contact with a user's skin) is increased with a dense plurality of discrete protrusions (see, e.g., FIGS. 10A-10N and 20A-24B) that can have any of a variety of shapes and sizes, though based on testing some are more effective than others. In some variations, these discrete protrusions can be cone-shaped, mound-shaped, and/or pyramid-like shaped, though other shapes are possible as well. In some variations, referring to FIG. 9A, alternating rows of cones/mounds are staggered with respect to adjacent rows in order to be able to pack in more such heat-dissipation-enhancement protrusions on the aluminum substrate 5. Conversely, referring to FIG. 9B, in other embodiments, the rows of heat-dissipation-enhancing protrusions are not staggered.

In another embodiment, the aluminum substrate 5 is substantially manufactured by a stamping process wherein a plurality of said heat-dissipation-enhancing surface protrusions are present on one side (and are substantially hollowed-out from the stamping process) while the other side, adapted to make contact with tissue, presents a plurality of voids/holes as a result of the manufacturing process. In this variation, said voids/holes aid in aeration of wounds and this type of topography is especially effective for enhancing thermal convection processes for cooling wounds.

In variations, each of the plurality of discrete heat-dissipation-enhancing protrusions and/or ridges is separated along the base plane of the aluminum substrate 5 by a distance. The separation distance used impacts the overall flexibility of the aluminum substrate, as well as the heat-dissipation effectiveness because as the distance increases, fewer discrete heat-dissipation-enhancing protrusions and/or ridges can populate the aluminum substrate 5. In various embodiments, the separation distances generally range between 0 (zero) and 0.5 mm, but can be increased in other applications. It should be appreciated by those skilled in the art that as the separation distance decreases and as the angle incline of the adjacent discrete protrusions increases, then the concave flexibility of the aluminum substrate 5 is adversely impacted.

Referring to FIGS. 16-19, in a variation, a plurality of rows of aeration holes 95 are disposed between rows of heat-dissipation-enhancement protrusions or ridges. In another variation, a plurality of rows and columns of aeration holes 95 are disposed between rows and columns of heat-dissipation-enhancement protrusions. In some embodiments, the manufactured aeration holes are 0.2 mm in diameter, with other variations using aeration holes with diameters that range in size from 0.1 to 0.3 mm. In variations, the spacing between the manufactured aeration holes, which inherently correlates to the number of manufactured aeration holes provided over an entire aluminum substrate 5, strikes a balance the efficacy of the healing effects of the bandage 10 and concerns over the structural integrity of the aluminum substrate. If too many manufactured aeration holes of a given size are placed too close together in a row, then the aluminum substrate 5 could have some weak points subject to easy tearing. In general, such aeration holes are equi-spaced between the heat-dissipation-enhancement protrusions or ridges, with sufficient space between the aeration holes so that the aluminum substrate 5 can flex along a line of said aeration holes without tearing the substrate material between the holes. In the case of relatively small-sized bandages 10, a common spacing between the aeration holes is about 4 mm. For relatively medium-sized bandages, a common spacing between the aeration holes is about 6 mm. For relatively large bandage applications, a common spacing between the aeration holes is about 8 mm. It should be appreciated by those skilled in the art that the aforementioned aeration hole spacing are exemplary only, and the needed spacing distances can vary according to a variety of factors, including the exact aluminum alloy used, whether any strain hardening or annealing processes occurred on the alloy, etc.

Figure 24A:
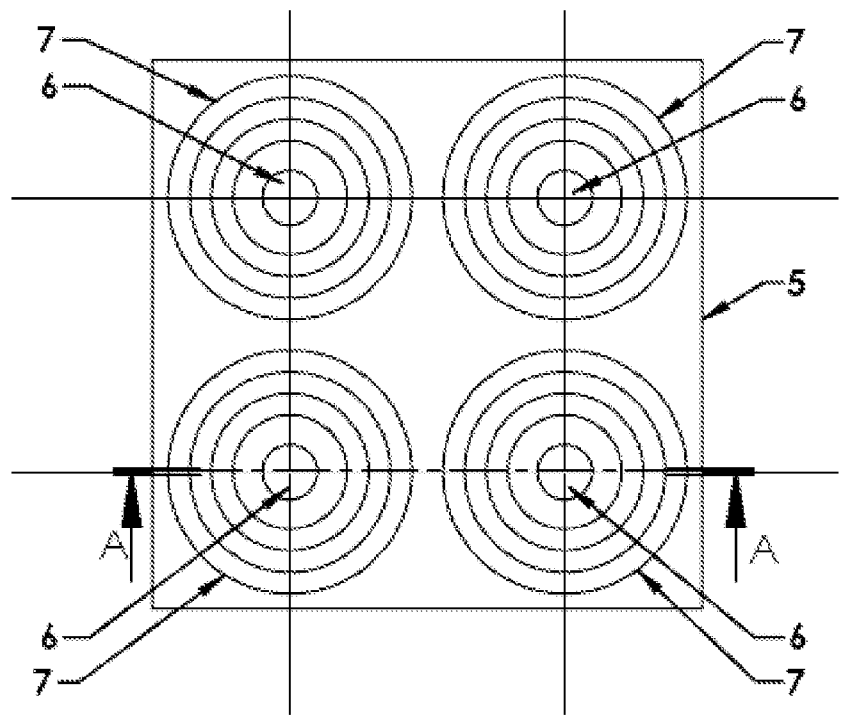
FIGS. 24A and 24B depict one embodiment of a top and side-cutaway view, respectively, of a small portion of a thermally conductive, metal-based substrate that can be used in Aluminaid™ bandage, showing a variation of the top-side topography that features a field of heat-dissipation-enhancing cone-like protrusions with holes disposed at the top of each protrusion. In this embodiment, it can be seen that the holes in the heat-dissipation-enhancing protrusions are narrower at the top of each respective protrusion, while widening as the bottom surface of the substrate is reached. The holes extend completely through the substrate, which helps aerate wounds as well as increase the amount of exposed surface area available to enhance thermal-convection processes.
Figure 24B:
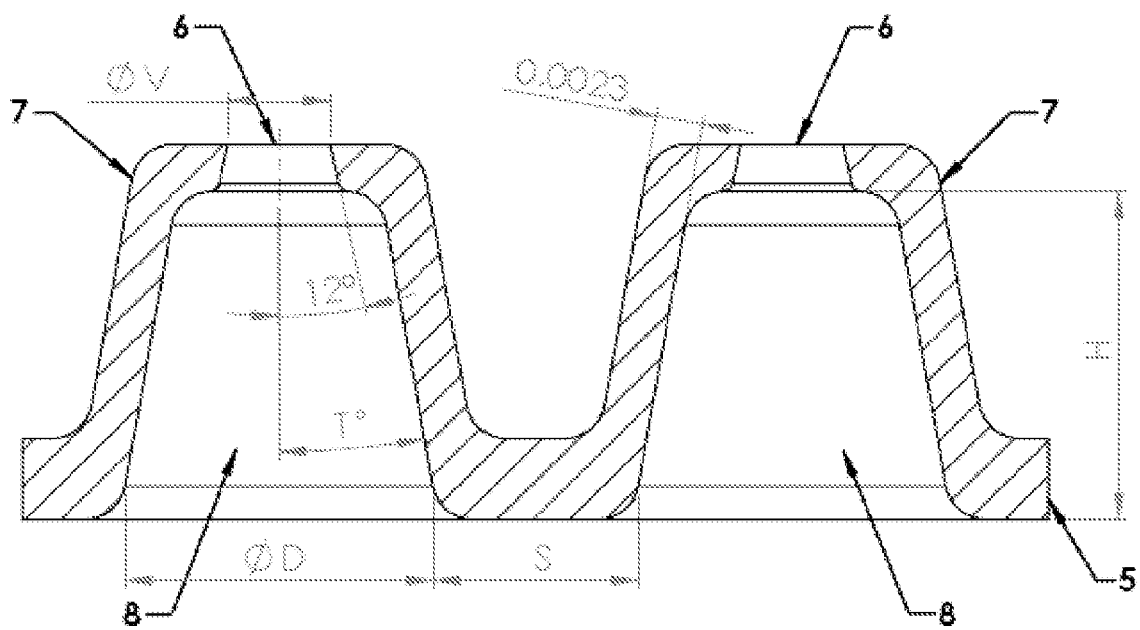
Figure 25:
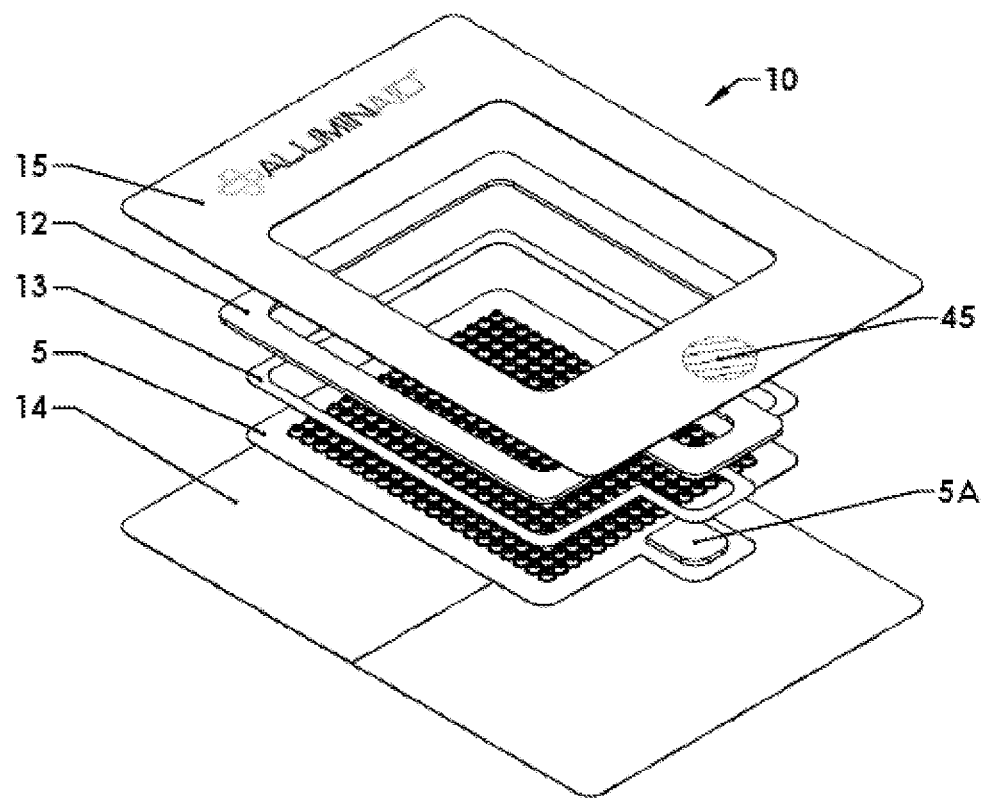
FIG. 25 depicts one form factor of one embodiment of an exploded view of an Aluminaid™ bandage, including an outer polymeric layer, an intermediate absorbent layer, a transfer adhesive layer, a thermally conductive, metal-based substrate layer, and a removable backing layer for protecting the adhesive material disposed about the outer perimeter of the bandage until ready for application to a wound.
Figure 26:
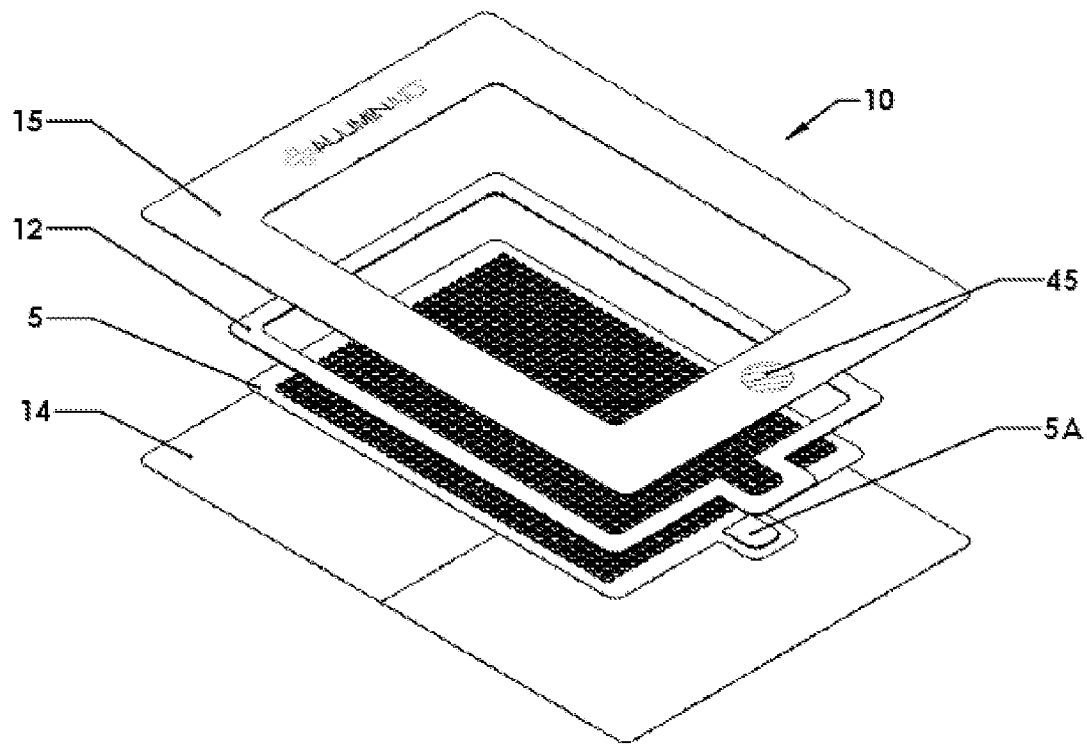
FIG. 26 depicts one form factor of one embodiment of an exploded view of an Aluminaid™ bandage, including an outer polymeric layer, an intermediate absorbent layer, a thermally conductive, metal-based substrate layer, and a removable backing layer for protecting the adhesive material disposed about the outer perimeter of the bandage until ready for application to a wound.
Figure 27:
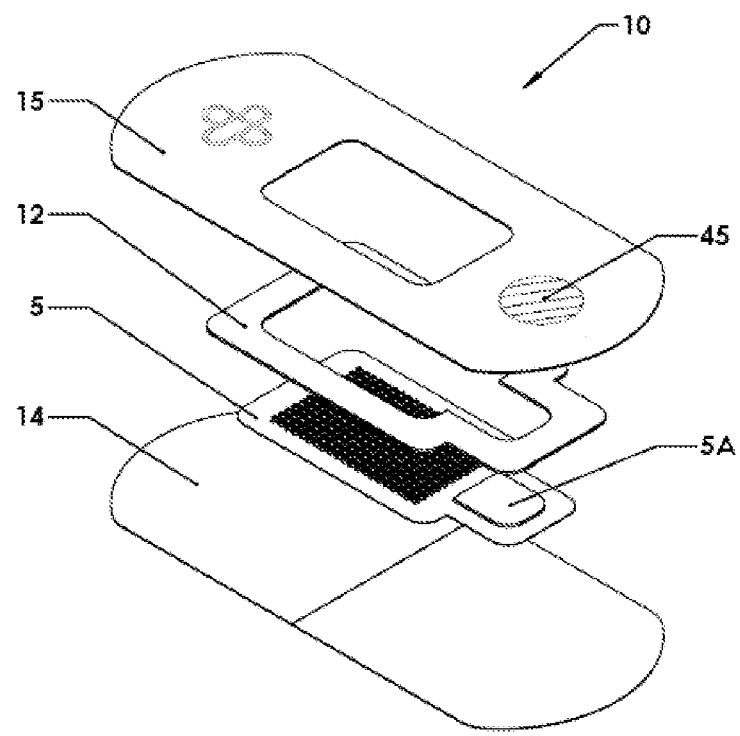
FIG. 27 depicts one form factor of one embodiment of an exploded view of an Aluminaid™ bandage, including an outer polymeric layer, an intermediate absorbent layer, a thermally conductive, metal-based substrate layer, and a removable backing layer for protecting the adhesive material disposed about the outer perimeter of the bandage until ready for application to a wound.
Figure 28:
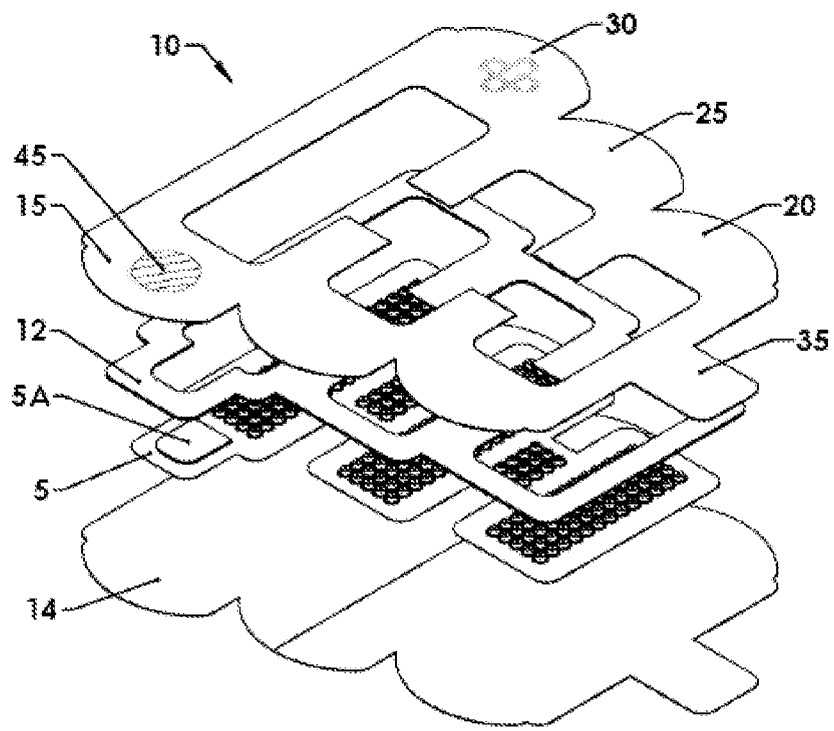
FIG. 28 depicts one embodiment of an exploded view of a finger-form-factor Aluminaid™ bandage, including an outer polymeric layer, an intermediate absorbent layer, a thermally conductive, metal-based substrate layer, and a removable backing layer for protecting the adhesive material disposed about the outer perimeter of the bandage until ready for application to a wound.
Figure 29:
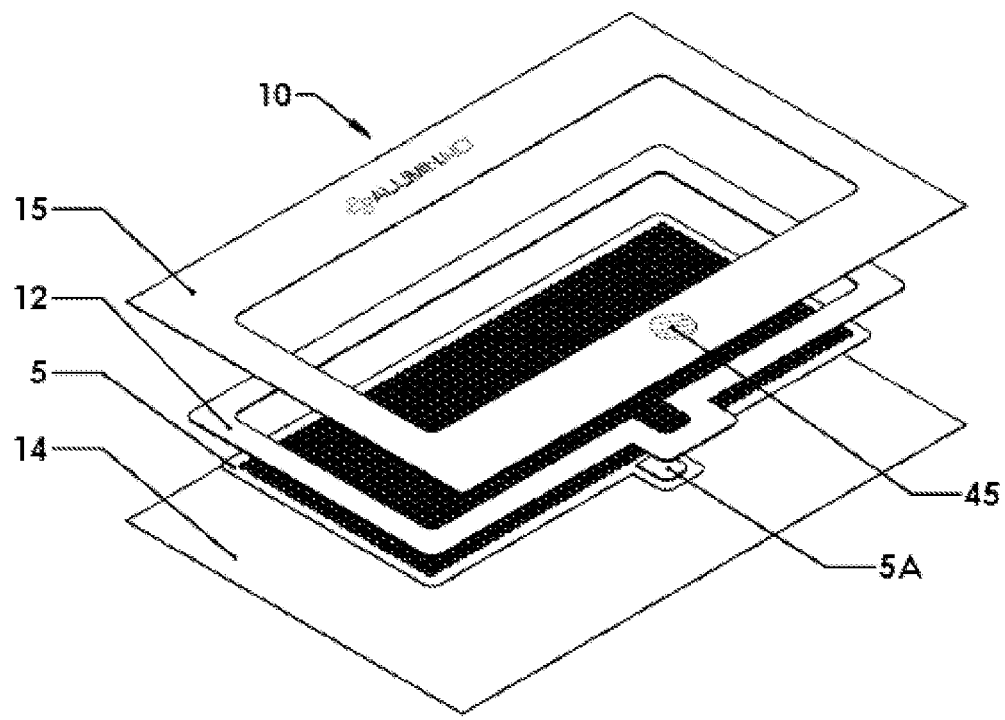
FIG. 29 depicts one form factor of one embodiment of an exploded view of an Aluminaid™ bandage, including an outer polymeric layer, an intermediate absorbent layer, a thermally conductive, metal-based substrate layer, and a removable backing layer for protecting the adhesive material disposed about the outer perimeter of the bandage until ready for application to a wound.
Figure 30:
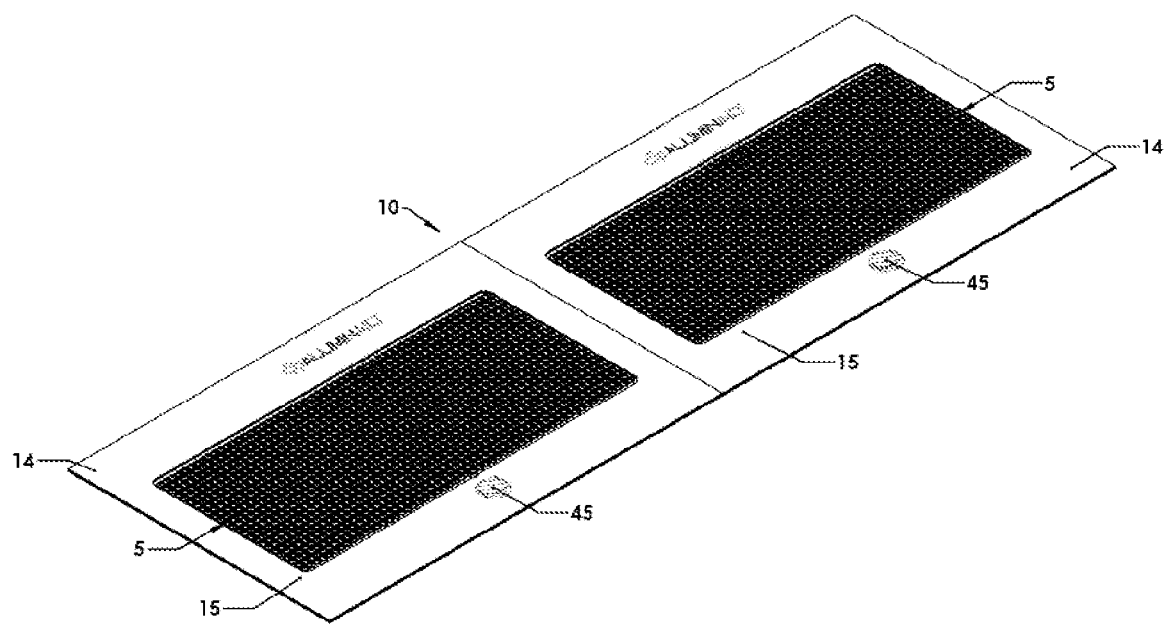
FIG. 30 depicts one embodiment of a portion of a continuous strip of multiple copies of the Aluminaid™ bandage embodiment depicted in FIG. 29, coupled together, whereby users can tear-off the length of bandage required and wrap the user-sized bandage strip around/over the wound area.
Figure 31A:
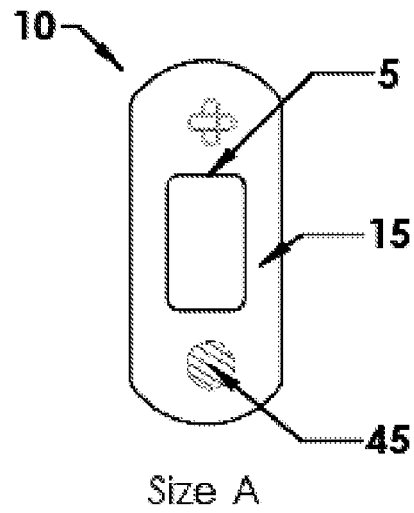
FIGS. 31A-31G depict various embodiments of the top-view of different Aluminaid™ bandage sizes and shapes. However, no attempt is made to depict any aluminum-substrate topography details in these figures.
Figure 31B:
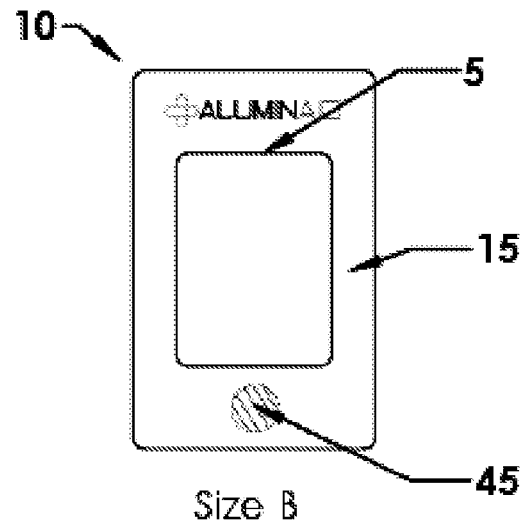
Figure 31C:
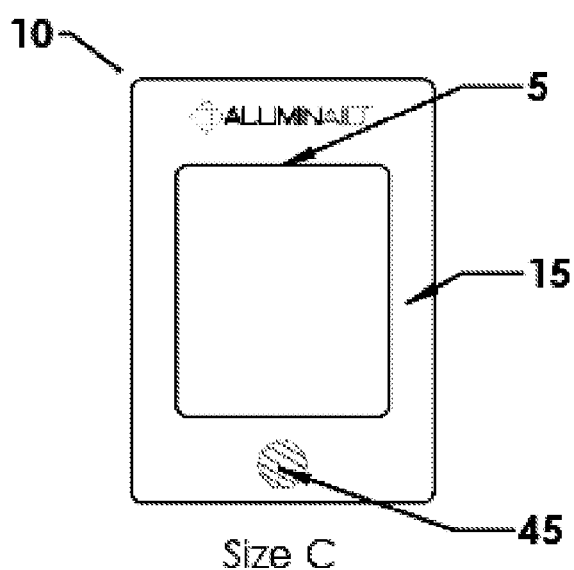
Figure 31D:
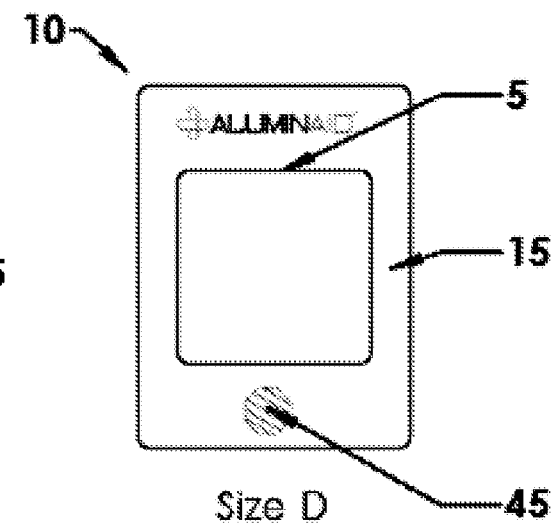
Figure 31E:
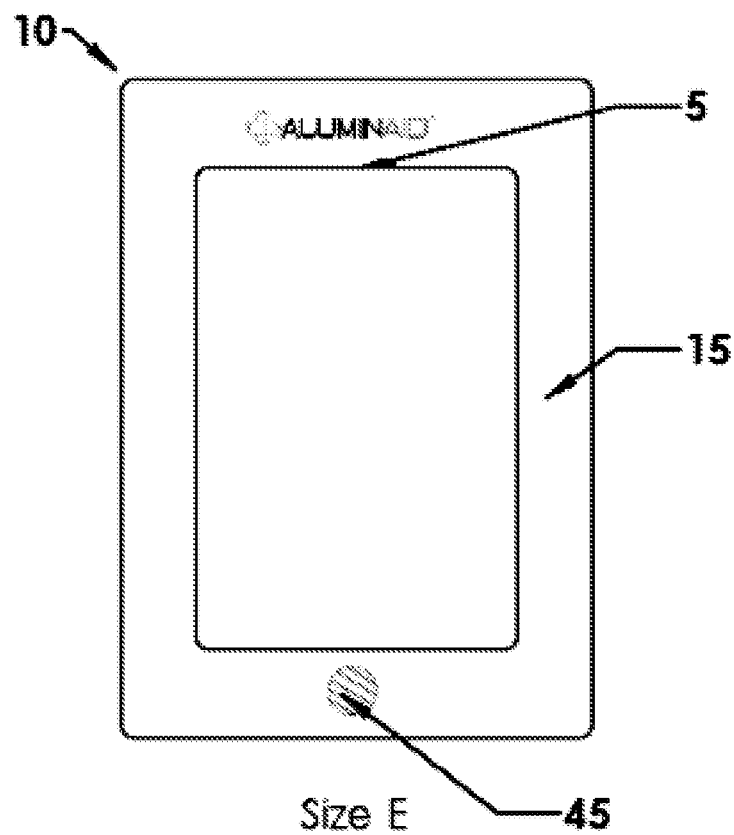
Figure 31F:
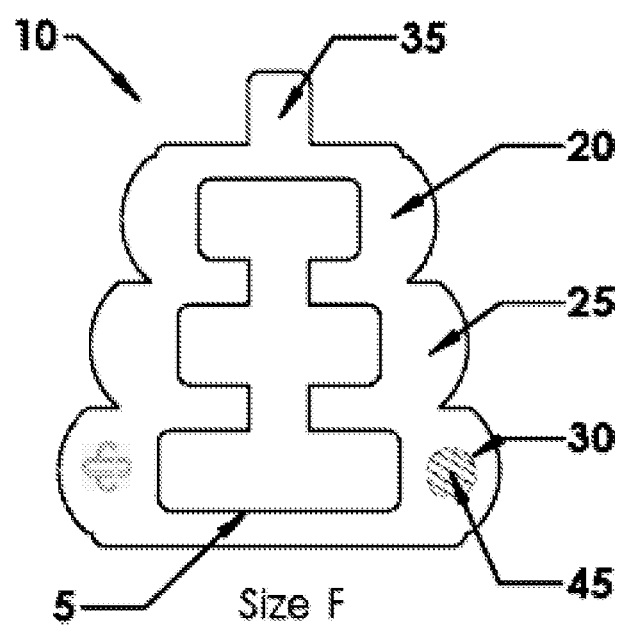
Figure 31G:
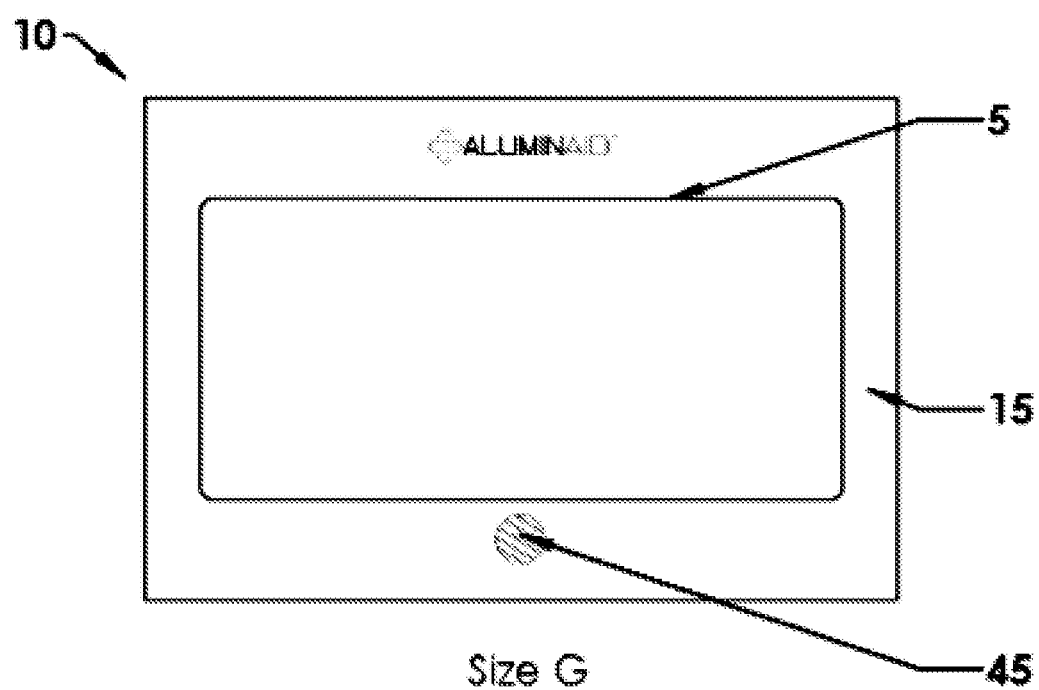

In yet another variation, referring to FIGS. 10J-10N and 20A-24B, the some or all of the plurality of discrete protrusions on the aluminum substrate include a hole in the middle of the protrusion. In some versions of this, the protrusion's central hole is a tapered hole and extends all the way through the aluminum substrate, thereby providing a strategically sized and placed aeration hole to aid in burn-wound healing, while also increasing the amount of surface area available for thermal convection to the ambient air. In other versions, the protrusions are formed by way of a stamping process that also puts a hole at the top of each protrusion so as to effectively make each protrusion substantially hollowed-out; that is a reverse taper as compared to the previously described version. (See e.g., FIGS. 20A-24B.) In addition, the presence of a substantial hole into the body of the protrusions also provides an even greater increase in the amount of protrusion surface area available for thermal-convection processes. An example of the dimensions "S", "D", "H", "T", and "V" for such hollowed-out protrusions, as depicted in FIGS. 24A-24B, are provided in Table 2:

TABLE 2

Exemplary Dimensions for
Hollowed Heat-Dissipation-Enhancing Protrusions
With Aeration Holes Disposed Through the Protrusions

| Variation | "S" | "D" | "H" | "T" | "V" |
|---|---|---|---|---|---|
| A | 0.010" | 0.015" | 0.016" | 10°/s | 0.005" |
| B | 0.015" | 0.020" | 0.030" | 15°/s | 0.005" |
| C | 0.20" | 0.025" | 0.030" | 10°/s | 0.008" |
| D | 0.030" | 0.020" | 0.040" | 10°/s | 0.005" |

It should be noted by those skilled in the art that the four examples in Table 2 are exemplary only, and that such hollowed-out, aerating heat-dissipation-enhancing protrusions can be fabrics to other dimensional specifications.

Many of the variations described herein, especially in Table 2, supra, as well as in FIGS. 20A-31G, were subjected to significant analysis and testing, including finite element method (FEM) analysis to develop optimum substrate topographies and geometries. Some of said testing is described in U.S. Patent Application No. 61/670,090, filed on Jul. 10, 2012, for "Thermally Conductive, Metal-Based Bandages to Aid in Medical Healing and Methods of Use", which is incorporated by reference.

In still more variations, referring to FIGS. 11A-12B, a dense plurality of corrugations or ridges 50, 55 are provided on the outer surface of the aluminum substrate 5 to enhance the heat-transfer/dissipation capabilities of the aluminum substrate 5. However, because in some embodiments the aluminum substrate 5 material can be strain hardened, especially in the thicker (corrugated) regions of the aluminum substrate 5, bandages using such corrugations/ridges may not be optimally flexible along the axis parallel with the rows of ridges/corrugations. This renders a bandage less useful for application to various parts of the body as it may be more difficult for a user to conform a bandage's aluminum substrate 5 to a particular part of a user body without overly stressing the aluminum substrate 5 along the longitudinal axis of the ridges, thus compromising the integrity and possible effectiveness of the bandage 10.

In some embodiments, a plurality of pyramid-shaped, cone-shaped, and/or dome-shaped protrusions manufactured in the aluminum substrate 5 is preferred over corrugations/ridges because, while the available outer surface area for heat-dissipation enhancement is largely equal between the two solutions (assuming equivalent widths and peak heights), an aluminum substrate with a plurality of non-ridge-like protrusions is more flexible along multiple axes. This is important because it furthers the goal of being able to readily apply bandages 10 to a wide variety of body applications and form factors.

It should be appreciated by one ordinarily skilled in the art that number, size/dimensions, and shape of the heat-sink protrusions and/or corrugations depicted in FIGS. 1A-31G are merely exemplary, and that many other shapes and sizes of cone-like or ridge-like structures (or similarly effective geometric structures) could be used for the aluminum substrate 5 in order to enhance the heat transfer of the bandage 10.

In yet more variations, a thermally conductive adhesive, paste, gel, or grease is applied to the area of a user's skin to enhance the heat transfer from a burn wound to the aluminum substrate heat sink 5. In some of these variations, the thermally conductive compound is derived from metal or silicone (usually with a zinc-oxide or aluminum-oxide inclusion to improve conductivity), and essentially fills gaps where air would normally be present. The thermally conductive compound provides a superior conductor (as compared to air) almost equal to that of the conductor (the aluminum substrate 5) itself. The performance of thermally conductive compound is measured in W/m-K. Standard silicon/zinc-oxide thermal compound has thermal conductivities in the range of 0.7-0.9 W/m-K.

In such variations, the thermally conductive medium used can also be an aluminum-infused medicinal/therapeutic cream, ointment, or other compound.

In more variations, the second, polymeric, outer layer 15 of the bandage 10 is coupled about the periphery of the aluminum substrate 5, yet leaves most of the top surface of the aluminum substrate 5 uncovered so as to better allow heat thermally conducted from a burn wound through the aluminum substrate 5 to dissipate via thermal convection and/or radiation to the ambient air.

In some alternate variations, a roll or sheet of aluminum substrate 5 is used without a coupled second layer 15, wherein the aluminum substrate is applied over a burn wound, and is fixed into place around the edges of the application with medical tape or gauze, while leaving most of the aluminum substrate 5 open to the air to facilitate heat dissipation.

Table 3 provides a list of some example form-factor dimensions used in some embodiments. It should be noted that this list is exemplary only, and is not intended to limit the scope of the inventive disclosure herein in any way.

TABLE 3

Exemplary Bandage Embodiment Dimensions

| Form Factor Embodiment | Polymer outer Base Size (mm x mm) | Aluminum Substrate Size (mm x mm) | Effective Cooling Area (mm²) | Figure References |
|---|---|---|---|---|
| Narrow Bandage Strip | 25.4 x 76.2 | 20.3 x 35.5 | 714 | 3A-4B; 13A-15; 18-19; 27; 31A |
| Rounded Rectangle | 52.1 x 76.2 | 43.2 x 50.8 | 2185 | 1A-2B; 11A-11B; 16-17; 25-26; 31B-31E |
| Rounded Rectangle | 63.5 x 88.9 | 50.8 x 63.5 | 3229 | 1A-2B; 11A-11B; 16-17; 25-26; 31B-31E |
| Rounded Rectangle | 57.2 x 76.2 | 45.72 x 54.6 | 2500 | 1A-2B; 11A-11B; 16-17; 25-26; 31B-31E |
| Rounded Rectangle | 95.25 x 133.4 | 69.9 x 101.6 | 7099 | 1A-2B; 11A-11B; 16-17; 25-26; 31B-31E |
| Finger-Form | 85.1 x 93.4 | 58.4 x 69.9 | 2885 | 5A-6B; 28; 31F |

In still more embodiments, the substantially polymeric and porous second layer 15 of the bandage 10 incorporates a thermochromic compound 40, 45, 70, or 80 (similar to what is typically found in mood rings) so that a user can actually see a visual indicator of the heat being removed from the user's skin/burn. In a variation, referring to FIGS. 13A-13B and 25-29, the top side of the aluminum substrate 5 has an extended member 5A that extends under the second layer 15 to be under and in direct contact with the thermochromic compound 40, 45, wherein the aluminum extension 5A provides thermal communication between a burn wound (via the aluminum substrate 5) and the thermochromic compound 40, 45. In another variation, referring to FIG. 14, the top, exposed textured side of the aluminum substrate 5 (that is, the heat-dissipation-enhancing topography side) has one or more thin aluminum strips 75 that are used to support and position a thermochromic indicator member 70 over the exposed top side of the aluminum substrate 5. In still more variations, referring to FIG. 15, a small subset of the heat-dissipation protrusions on the top side of the aluminum substrate 5 are coated at their tip with thermochromic compound 80. In other variations, referring to FIGS. 16-19, the top side of the aluminum substrate 5 has a thermal-communication member 90 that extends to the thermochromic indicator 85, wherein the thermal-communication member 90 provides thermal communication between a burn wound (via the aluminum substrate 5) and the thermochromic indicator 85. In some embodiments, the thermal-communication member 90 can be an etched line of thermochromic paint or can be an aluminum conduit.

In some embodiments, the thermochromic indicators 40, 45, 70, 80, 85 have compounds calibrated to indicate when a burn is sufficiently cooled (in some cases providing a color indicator; e.g., "green"; and/or an icon indicator; e.g., a "smilie face") or still too warm (in some cases providing a color indicator; e.g., "red"; and/or an icon indicator; e.g., a "frownie face"). In more variations, the thermochronic indicator 45 is in thermal communication with the aluminum substrate 5 via a thermally conductive extension 5A and will change color on the end that is more proximate to the aluminum substrate 5 more quickly than on the other end of the thermochromic indicator 45 because of the thermal strata. Such stratification of the color change of the thermochromic indicator 45 helps a user gauge the rate and amount of cooling.

As an example, a user might apply an Aluminaid™ bandage 10 to a burn from a hot pan, and initially, the user can see a red iconic thermochromic indicator 40, 70, 80, which indicates that a user should keep the Aluminaid™ bandage 10 in place. Later, the pain subsides and the burned tissue cools, the user can see a green iconic thermochromic indicator 45, 70, 80, 85, which indicates to the user that the Aluminaid™ bandage 10 can be safely changed out to a traditional medical dressing.

C. Details of Aluminaid™ Bandage Materials
Refer to FIGS. 1A-31G.
Aluminum

In many embodiments of bandages assuming a specific form factor (e.g., a finger-form-factor dressing, FIGS. 5A-6B, 28, and 31F), the first bandage layer 5 disposed to make direct contact with the burn wound covers approximately 30-100% of the entire length of the bandage 10. The outer edges of the product are reserved for a suitable adhesive which forms the bond between the outer sheath (cotton wool or polymer) and the aluminum dressing.

The aluminum material used in the substrate 5 is generally comprised of at least 90% aluminum, and is essentially an amphoteric material. Other composites can occur as a result of naturally occurring processes and sometimes some contamination during manufacture. However, none of these other additional substances are toxic in-relation to the scope of the prescribed application. In some embodiments, the aluminum material is annealed in order to make the material more ductile to better facilitate various form factors. The annealing process includes gauging the aluminum substrate 5 and specifically annealing it to enhance ductility in order to optimally navigate the contours of body parts (e.g., finger and hands, but not excluding general-purpose forms, such as rectangle and square-shaped dressings).

In variations, the aluminum may be subjected to electroplating or other non-toxic coating in order to facilitate ductility, improve performance, and enhance durability.

When aluminum combines with oxygen, the two elements undergo a spontaneous reaction:

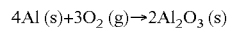

$$4Al\,(s)+3O_2\,(g)\rightarrow 2Al_2O_3\,(s)$$

The properties of the aluminum used in some embodiments of the Aluminaid™ bandages and wraps can be summarized as follows:

Main Composite: ≧90% aluminum, but is preferred to be ≧99% aluminum
In some embodiments, the aluminum used is an alloy comprised of ≧92% aluminum and approximately 5% magnesium, with the balance of the alloy being naturally occurring impurities. This alloy is especially suited for a proprietary annealing process designed to enhance the ductility of the aluminum substrate used in bandages, discussed infra.
The atomic weigh of the aluminum used is approximately 26.98 AMU.

Form: Solid with specifically formed ridges to maximize the available heat-transfer surfaces for cooling a wound.

Annealed: Yes, in order to optimally navigate the contours of body parts (e.g., fingers and hands, but not excluding general-purpose forms, such as rectangle and square-shaped dressings). In some embodiments, a proprietary annealing process is used, as discussed infra.

Thickness: ≦1 mm, as measured from the bottom of the aluminum substrate to the average peak height of the plurality of heat-dissipation-enhancement protrusions/ridges on the top side of the substrate. In areas of the substrate between such heat-dissipation-enhancement protrusions/ridges, the thickness is ≦0.1 mm.

Thermal Conductivity: approximately 209 W/m·k±10%.

Density: ≧2.699 g/cm³.

Metallurgical Index: 8217

Toxicity: Non-toxic (aluminum-oxide layer coating)

Porosity: Defined as sufficient to enable the administration of a controlled release remedial substance, and/or to enable paths for oxygen to be introduced to a burn wound. The aluminum foil used must not exceed the defined thickness needed to ensure that the foil does not become impermeable to oxygen. Porosity can be obtained by either the inherent by-product of the aluminum-rolling process, or by mechanically introducing pinholes. Section III.B, supra, discusses some strategies for mechanically introducing aeration holes in the aluminum substrate beyond those that normally occur as a by-product of the manufacturing process.

Recycle: The aluminum alloy used in the substrate 5 can be recycled and can be made of recycled aluminum alloy.

Annealing of Aluminum
In some embodiments, the aluminum substrate 5 is subjected to an annealing process to enhance the ductility and flexibility of the aluminum substrate as it is applied to various parts of a user body. It is a heat treatment used to soften the aluminum alloys to that they can be easily worked and formed. The annealing process gives the resultant alloy a temper designation of "0", which is very soft. In a variation, instead of quenching the aluminum material immediately after heating (as in the solution heat treatment of aluminum process), the aluminum material is cooled in stages at specified temperatures.

In a specialized embodiment, an aluminum alloy comprised of approximately 92% aluminum and approximately 5% magnesium is used (with the remainder of the constituents being naturally occurring impurities). Magnesium is added to the alloy because of its curative elements, its non-toxicity, and reasonable thermal conductivity (even though it is less than aluminum, it will not significantly degrade the alloy's overall thermal conductivity).

In a variation, the Aluminum-magnesium alloy is annealed to condition "1100-0". It is annealed for approximately one hour at a temperature range of 775° C.-900° C. In some embodiments, the annealed aluminum alloy is furnace cooled. However, in another embodiment, the aluminum alloy is then allowed to naturally cool; that is, non-furnace cool, thereby substantially removing any strain hardening. The aluminum alloy re-crystallizes during this natural cooling process such that there is greater consistency in the direction of grain growth (that is, most, if not all, of the grains are oriented in a uniform direction), giving the material dramatically greater ductility. These specialized fabrication techniques result in a reduced resistance to thermal conductivity, or greater thermal-conductivity gain, as well as better malleability (less structural resistance at the atomic level). This re-crystallized aluminum alloy is used in some embodiments as the primary material for the aluminum substrate 5 in Aluminaid™ bandages and wraps.

Perimeter Polymer Covering

In some embodiments of bandages 10, one or more edges of the aluminum substrate 5 are coupled to a second layer 15 which extends beyond the boundaries of the aluminum substrate 5 and typically has adhesive material disposed on its bottom surface to facilitate coupling to a user's skin. A selection of materials commonly used in medical bandages may be used as an effective second layer 15, but a perforated polymer such as 1527-ENP ethylene vinyl acetate (EVA) is preferred in many embodiments.

In another embodiment, the second layer 15 is comprised of 3M™ Transpore™ Tape.

In many variations, the adhesive compound disposed on the exposed bottom side of the second layer 15 can be comprised of any non-toxic medical adhesive commonly used in the art, and in most variations, the bandage is stored with a peelable backing layer 14 detachably coupled to the adhesive on the second layer 15.

Thermochromic Compounds

In some variations, the incorporated thermochromic materials 40, 45, 70, 80, 85 used in the outer bandage layers are comprised of thermochromic liquid crystals (for example, but not limited to, cholesteryl ester carbonates, chiral nematic (non-sterol) aryl compounds, and (2-methylbutyl)phenol 4-alkyl(oxy)benzoates) and/or leuco dyes/inks (for example, but not limited to, spirolactones, fluorans, spiropyrans, and fulgides). In even more variations, the thermochromic-impregnated bandage materials are calibrated to display a "neutral" color at the average human skin temperature; that is, approximately 98.6° F. (37.0° C.).

In other variations, the thermochromic indicator materials 40, 45, 70, 80, 85 used can be a paint, a gel, or a thermochromic-compound-impregnated polymer.

In an embodiment, the thermochromic indicator material 40, 45, 70, 80, 85 comprises liquid crystals calibrated to display a green color indicator when the associated aluminum substrate has cooled to a predetermined threshold, and also comprises liquid crystals calibrated to display a red color indicator when the associated aluminum substrate exceeds a predetermined threshold.

IV. A Bandage for a Burn Wound Embodiment

In one embodiment, the inventive concept is directed to a bandage that is adapted to treat a burn wound. Refer to FIGS. 1A-31G, with an emphasis on FIGS. 20A-31G. In an embodiment, the bandage 10 comprises a first layer 5, substantially comprised of a thin thermally conductive metal substrate 5, having a first surface and a second surface, wherein the metal substrate's first surface has a profile, when viewed from the side, that is substantially flat and is adapted to make direct contact with a burn wound, and most of the metal substrate's second surface has a non-flat, heat-dissipation-enhancing surface topography, when viewed from the side, that rises above the base plane of the aluminum substrate 5, adapted to be directly exposed to air. In variations, the thermally conductive metal substrate 5 is substantially comprised of a metal selected from the group consisting of aluminum, silver, gold, copper, magnesium, tungsten, platinum, and a metal alloy substantially based on any other aforementioned metals.

In another variation, the bandage 10 is further comprised of a second outer layer 15, substantially comprised of a substantially polymeric material, and a third intermediate layer 12, substantially comprised of absorbent material, each layer having a first surface and a second surface. In more variations, the third intermediate absorbent layer's 12 first surface is adapted to mate with and cover at least two of the perimeter edges of the second surface of the first layer 5, but leaving most of the first layer's 5 second surface uncovered and exposed to the air, wherein:

The second outer layer's 15 first surface is adapted to mate with and cover at least two of the perimeter edges of the second surface of the third layer 12, but also leaving most of the first layer's 5 second surface uncovered and exposed to the air;

The second and third layers 15, 12 extend beyond at least two perimeter edges of the first layer 5;

The second outer layer 15 extends beyond the at least two perimeter edges of the third intermediate layer 12;

The at least two perimeter edges of the first layer 5 are bonded to a portion of the first surface of the third intermediate layer 12;

The at least two perimeter edges of the third intermediate layer 12 are bonded to a portion of the first surface of the second outer layer 15, The remainder of the first surface of the second outer layer 15 is substantially coated with a non-toxic adhesive material adapted for use on user skin; and The first, second, and third layers 5, 15, 12 are sized and shaped to a form factor that is adapted to one or more areas of a user body.

In an alternative variation, the bandage 10 can be fabricated without the absorbent, third intermediate layer 12, wherein the second outer layer 15 extends beyond at least two perimeter edges of the first layer 5, and at least two edges of the first surface 5 are bonded to a portion of the first surface of the second outer layer 15. This variation would facilitate better overall heat-transfer properties of the bandage 10, though the lack of absorbent material about the perimeter of the bandage 10 may not be as desirable for oozing wounds.

This embodiment can be further enhanced wherein the non-flat, heat-dissipation-enhancing surface topography 5 includes a plurality of heat-dissipation-enhancing protrusions 7 (also, see, e.g., FIGS. 10A-10N), said protrusions selected from the group consisting of cone-like protrusions, half-dome-like protrusions, and pyramid-like protrusions. In variations, the plurality of heat-dissipation-enhancing protrusions 7 (also see, e.g., FIGS. 10A-10N) are disposed in rows on the first layer 5, the positioning of every row with respect to its adjacent row(s) is selected from the group consisting of staggered and non-staggered. In yet another variation, at least one heat-dissipation-enhancing protrusion 7 has a hole 6 disposed from its apex toward the base plane of the thermally conductive metal substrate 5, which aids in the bandage's 10 thermal convection processes because of the added exposed surface area to air. In other variations, the first layer 5 includes a plurality of manufactured aeration holes 6 in the thermally conductive metal substrate 5. In some applications, the at least one heat-dissipation-enhancing protrusion 7 with a hole 6 disposed from its apex toward the base plane of the thermally conductive metal substrate 5 has its hole extending all the way through the thermally conductive metal substrate 5. In some cases, the hole 6 disposed in at least one heat-dissipation-enhancing protrusion 7 has a diameter that is narrower toward the second surface of the first layer 5 and wider toward the first surface of the first layer, which both aids in the thermal-convection properties of the substrate 5 and is formed by way of a two-step manufacturing stamping process wherein the main protrusion 7 are formed by a first stamping of the substrate 5 from the first surface toward the second surface, then a second stamping/punching at the apex of the formed protrusions 7 toward the first surface of the substrate 5 to form the openings 6. In some other cases, the holes 6 in the formed protrusions 7 are cylindrical in shape, maintaining approximately the same diameter along the length of the hole 6.

This embodiment can be enhanced wherein the material in the thermally conductive metal substrate 5 is comprised of an aluminum alloy containing at least 92% aluminum and about 5% magnesium.

This embodiment can be enhanced wherein the aluminum alloy used in the first layer 5 is annealed by a process comprised of the steps of:
Subjecting the aluminum alloy to a temperature in the range of 775° C. to 900° C.; and
Either subjecting the annealed aluminum alloy to furnace cooling or allowing the aluminum alloy to naturally cool; that is, non-furnace cool. It should be noted, however, that the natural cooling step results in substantially removing any strain hardening of the aluminum alloy and ensuring that the re-crystallization of the aluminum alloy results in substantially uniform grain growth and directional orientation.

This embodiment can be further enhanced by further comprising a thermochromic indicator member 45, wherein the thermochromic indicator member 45 is in thermal communication 5A with a burn wound via the first layer 5, and the thermochromic indicator member 45 is comprised of material calibrated to:
indicate to a user when a burn on which said bandage is applied is still too warm for safe removal of said bandage, based on a predetermined threshold, and
indicate to a user when a burn has cooled to at least a predetermined threshold such that said bandage can be safely removed and/or changed-out for a new medical dressing.

In variations, the thermochromic indicator member 45 provides color-based user indications as to the thermal status of the burn to which said bandage is applied. In other variations, the thermochromic indicator member 45 provides icon-based user indications as to the thermal status of the burn to which said bandage is applied. In some applications, the thermochromic indicator member 45 is comprised of material selected from the group consisting of thermochromic liquid crystals, leuco dyes, and thermochromic inks.

This embodiment can be further enhanced wherein the second layer 15 is substantially comprised of perforated 1527-ENP ethylene vinyl acetate (EVA).

This embodiment can be further enhanced wherein the third intermediate layer 12 is substantially comprised of a material selected from the group consisting of cotton cause, silk gauze, porous plastic gauze, and hydrogel.

This embodiment can be further enhanced wherein the form factor is adapted to facilitate bandage 10 application to a part of a human body selected from the group consisting of finger, thumb, toe, elbow, wrist, knee, ankle, foot, hand palm, and face. In variations, the form factor is of a shape selected from the group consisting of rectangle, square, rounded-corner rectangle, circle, oval, triangle, rounded-corner triangle, and continuous-strip roll.

V. A Method of Making a Bandage for a Burn Wound Embodiment

This embodiment is directed to a method of making a bandage adapted for treating burns and other wounds. Refer to FIGS. 1A-31G, with an emphasis on FIGS. 20A-31G. The method comprises the step of providing a first layer 5, substantially comprised of a thin thermally conductive metal substrate 5, having a first surface and a second surface, wherein the metal substrate's first surface has a profile, when viewed from the side, that is substantially flat and is adapted to make direct contact with a burn wound, and most of the metal substrate's second surface has a non-flat, heat-dissipation-enhancing surface topography, when viewed from the side, that rises above the base plane of the aluminum substrate 5, adapted to be directly exposed to air. In variations, the thermally conductive metal substrate 5 is substantially comprised of a metal selected from the group consisting of aluminum, silver, gold, copper, magnesium, tungsten, platinum, and a metal alloy substantially based on any other aforementioned metals.

In another variation, the method is further comprised of the steps of providing a second outer layer 15, substantially comprised of a substantially polymeric material, and providing a third intermediate layer 12, substantially comprised of absorbent material, each layer having a first surface and a second surface. In more variations, the third intermediate absorbent layer's 12 first surface is adapted to mate with and cover at least two of the perimeter edges of the second surface of the first layer 5, but leaving most of the first layer's 5 second surface uncovered and exposed to the air, wherein:
The second outer layer's 15 first surface is adapted to mate with and cover at least two of the perimeter edges of the second surface of the third layer 12, but also leaving most of the first layer's 5 second surface uncovered and exposed to the air;
The second and third layers 15, 12 extend beyond at least two perimeter edges of the first layer 5;

The second outer layer 15 extends beyond the at least two perimeter edges of the third intermediate layer 12;

The at least two perimeter edges of the first layer 5 are bonded to a portion of the first surface of the third intermediate layer 12;

The at least two perimeter edges of the third intermediate layer 12 are bonded to a portion of the first surface of the second outer layer 15, The remainder of the first surface of the second outer layer 15 is substantially coated with a non-toxic adhesive material adapted for use on user skin; and The first, second, and third layers 5, 15, 12 are sized and shaped to a form factor that is adapted to one or more areas of a user body.

In an alternative variation, the bandage 10 can be fabricated without the absorbent, third intermediate layer 12, wherein the second outer layer 15 extends beyond at least two perimeter edges of the first layer 5, and at least two edges of the first surface 5 are bonded to a portion of the first surface of the second outer layer 15. This variation would facilitate better overall heat-transfer properties of the bandage 10, though the lack of absorbent material about the perimeter of the bandage 10 may not be as desirable for oozing wounds.

This embodiment can be further enhanced wherein the non-flat, heat-dissipation-enhancing surface topography 5 includes the manufacturing step of providing a plurality of heat-dissipation-enhancing protrusions 7 (also, see, e.g., FIGS. 10A-10N), said protrusions selected from the group consisting of cone-like protrusions, half-dome-like protrusions, and pyramid-like protrusions. In variations, the plurality of heat-dissipation-enhancing protrusions 7 (also see, e.g., FIGS. 10A-10N) are disposed in rows on the first layer 5, the positioning of every row with respect to its adjacent row(s) is selected from the group consisting of staggered and non-staggered. In yet another variation, at least one heat-dissipation-enhancing protrusion 7 is provided with a hole 6 disposed from its apex toward the base plane of the thermally conductive metal substrate 5, which aids in the bandage's 10 thermal convection processes because of the added exposed surface area to air. In other variations, the first layer 5 includes the step of providing a plurality of manufactured aeration holes 6 in the thermally conductive metal substrate 5. In some applications, the at least one heat-dissipation-enhancing protrusion 7 with a hole 6 disposed from its apex toward the base plane of the thermally conductive metal substrate 5 has its hole extending all the way through the thermally conductive metal substrate 5. In some cases, the hole 6 disposed in at least one heat-dissipation-enhancing protrusion 7 has a diameter that is narrower toward the second surface of the first layer 5 and wider toward the first surface of the first layer, which both aids in the thermal-convection properties of the substrate 5 and is formed by way of a two-step manufacturing stamping process wherein the main protrusion 7 are formed by a first stamping of the substrate 5 from the first surface toward the second surface, then a second stamping/punching at the apex of the formed protrusions 7 toward the first surface of the substrate 5 to form the openings 6. In some other cases, the holes 6 in the formed protrusions 7 are cylindrical in shape, maintaining approximately the same diameter along the length of the hole 6.

This embodiment can be enhanced wherein the material in the thermally conductive metal substrate 5 is comprised of an aluminum alloy containing at least 92% aluminum and about 5% magnesium.

This embodiment can be enhanced wherein the aluminum alloy used in the first layer 5 is annealed by a process comprised of the steps of:

Subjecting the aluminum alloy to a temperature in the range of 775° C. to 900° C.; and Either subjecting the annealed aluminum alloy to furnace cooling or allowing the aluminum alloy to naturally cool; that is, non-furnace cool. It should be noted, however, that the natural cooling step results in substantially removing any strain hardening of the aluminum alloy and ensuring that the re-crystallization of the aluminum alloy results in substantially uniform grain growth and directional orientation.

This embodiment can be further enhanced by further comprising the step of providing a thermochromic indicator member 45, wherein the thermochromic indicator member 45 is in thermal communication 5A with a burn wound via the first layer 5, and the thermochromic indicator member 45 is comprised of material calibrated to:

indicate to a user when a burn on which said bandage is applied is still too warm for safe removal of said bandage, based on a predetermined threshold, and indicate to a user when a burn has cooled to at least a predetermined threshold such that said bandage can be safely removed and/or changed-out for a new medical dressing.

In variations, the thermochromic indicator member 45 provides color-based user indications as to the thermal status of the burn to which said bandage is applied. In other variations, the thermochromic indicator member 45 provides icon-based user indications as to the thermal status of the burn to which said bandage is applied. In some applications, the thermochromic indicator member 45 is comprised of material selected from the group consisting of thermochromic liquid crystals, leuco dyes, and thermochromic inks.

This embodiment can be further enhanced wherein the second layer 15 is substantially comprised of perforated 1527-ENP ethylene vinyl acetate (EVA).

This embodiment can be further enhanced wherein the third intermediate layer 12 is substantially comprised of a material selected from the group consisting of cotton cause, silk gauze, porous plastic gauze, and hydrogel.

This embodiment can be further enhanced wherein the form factor is adapted to facilitate bandage 10 application to a part of a human body selected from the group consisting of finger, thumb, toe, elbow, wrist, knee, ankle, foot, hand palm, and face. In variations, the form factor is of a shape selected from the group consisting of rectangle, square, rounded-corner rectangle, circle, oval, triangle, rounded-corner triangle, and continuous-strip roll.

VI. A Method of Using a Bandage for a Burn Wound Embodiment

This embodiment is directed to a method of using a bandage according to either Section III or Section IV, supra, adapted for treating burns and other wounds. Refer to FIGS. 1A-31G, with an emphasis on FIGS. 20A-31G. It should be noted that this particular embodiment pertains to bandages without a second or third laser 15, 12. The method comprises the steps of:

Obtaining a bandage 10 according to either Section III or Section IV, supra; and Applying the bandage 10 to a burn wound 60 with the first surface of the first layer 5 in direct contact with said burn wound 60; and Securing the bandage 10 in position over the burn wound 60 by applying adhesive medical tape along some or all of the edges of the bandage 10 and extending to the tissue surrounding non-burned tissue, wherein the top side of the bandage first layer 5 is mostly left uncovered and exposed to the ambient environment.

This embodiment can be further enhanced wherein the non-flat, heat-dissipation-enhancing surface topography 5 includes a plurality of heat-dissipation-enhancing protrusions 7 (also, see, e.g., FIGS. 10A-10N), said protrusions selected from the group consisting of cone-like protrusions, half-dome-like protrusions, and pyramid-like protrusions. In variations, the plurality of heat-dissipation-enhancing protrusions 7 (also see, e.g., FIGS. 10A-10N) are disposed in rows on the first layer 5, the positioning of every row with respect to its adjacent row(s) is selected from the group consisting of staggered and non-staggered. In yet another variation, at least one heat-dissipation-enhancing protrusion 7 has a hole 6 disposed from its apex toward the base plane of the thermally conductive metal substrate 5, which aids in the bandage's 10 thermal convection processes because of the added exposed surface area to air. In other variations, the first layer 5 includes a plurality of manufactured aeration holes 6 in the thermally conductive metal substrate 5. In some applications, the at least one heat-dissipation-enhancing protrusion 7 with a hole 6 disposed from its apex toward the base plane of the thermally conductive metal substrate 5 has its hole extending all the way through the thermally conductive metal substrate 5. In some cases, the hole 6 disposed in at least one heat-dissipation-enhancing protrusion 7 has a diameter that is narrower toward the second surface of the first layer 5 and wider toward the first surface of the first layer, which both aids in the thermal-convection properties of the substrate 5 and is formed by way of a two-step manufacturing stamping process wherein the main protrusion 7 are formed by a first stamping of the substrate 5 from the first surface toward the second surface, then a second stamping/punching at the apex of the formed protrusions 7 toward the first surface of the substrate 5 to form the openings 6. In some other cases, the holes 6 in the formed protrusions 7 are cylindrical in shape, maintaining approximately the same diameter along the length of the hole 6.

This embodiment can be enhanced wherein the material in the thermally conductive metal substrate 5 is comprised of an aluminum alloy containing at least 92% aluminum and about 5% magnesium.

This embodiment can be enhanced wherein the aluminum alloy used in the first layer 5 is annealed by a process comprised of the steps of:
  Subjecting the aluminum alloy to a temperature in the range of 775° C. to 900° C.; and
  Either subjecting the annealed aluminum alloy to furnace cooling or allowing the aluminum alloy to naturally cool; that is, non-furnace cool. It should be noted, however, that the natural cooling step results in substantially removing any strain hardening of the aluminum alloy and ensuring that the re-crystallization of the aluminum alloy results in substantially uniform grain growth and directional orientation.

This embodiment can be enhanced wherein the bandage further comprises a thermochromic indicator member 45, wherein:
  The thermochromic indicator member 45 is in thermal communication 5A with a burn wound via the first layer 5, and
  The thermochromic indicator member 45 is comprised of material calibrated to indicate to a user when a burn on which the bandage 10 is applied is still too warm for safe removal of said bandage, based on a predetermined threshold, and indicate to a user when a burn has cooled to at least a predetermined threshold such that the bandage 10 can be safely removed and/or changed-out for a new medical dressing.

This embodiment can be enhanced wherein the thermochromic indicator member 45 provides color-based user indications as to the thermal status of the burn to which the bandage 10 is applied.

This embodiment can be enhanced wherein the thermochromic indicator member 45 provides icon-based user indications as to the thermal status of the burn to which the bandage 10 is applied.

This embodiment can be enhanced wherein the thermochromic indicator member 40, 45, 70, 80, 85 is comprised of material selected from the group consisting of thermochromic liquid crystals, leuco dyes, and thermochromic inks.

This embodiment can be enhanced by further comprising the steps of:
  Observing the thermochromic indicator member 45;
  If the thermochromic indicator member 45 indicates that the burn wound 60 is too warm, then continuing the application of the bandage 10 on the burn wound 60 to further cooling of the burn wound 60;
  If the thermochromic indicator member 45 indicates that the burn wound 60 has cooled sufficiently, then removing the bandage 10 from the burn wound 60 and applying a different medical dressing to the burn wound 60; and
  Repeating the previous steps as necessary until the bandage 10 has been removed from the burn wound 60.

This embodiment can be enhanced wherein the different medical dressing referred to above is any one or combination of dressings selected from the group consisting of medicinal compounds, therapeutic compounds, and sterile gauze-based or cotton-based bandages.

This embodiment can be further enhanced wherein the form factor is adapted to facilitate bandage 10 application to a part of a human body selected from the group consisting of finger, thumb, toe, elbow, wrist, knee, ankle, foot, hand palm, and face. In variations, the form factor is of a shape selected from the group consisting of rectangle, square, rounded-corner rectangle, circle, oval, triangle, rounded-corner triangle, and continuous-strip roll.

This embodiment can be enhanced by further comprising the step of subjecting the exposed aluminum substrate 5 of the applied bandage 10 to forced-air cooling in order to speed cooling of the burn wound 60.

VII. A Method of Using a Bandage for a Burn Wound Embodiment

This embodiment is directed to a method of using a bandage according to either Section III or Section IV, supra, adapted for treating burns and other wounds. Refer to FIGS. 1A-31G, with an emphasis on FIGS. 20A-31G. It should be noted that this particular embodiment pertains to bandages with at least a second layer (and possibly a third layer) 15, 12. The method comprises the steps of:
  Obtaining a bandage 10 according to either Section III or Section IV, supra; and
  Applying the bandage 10 to a burn wound 60 with the first surface of the first layer 5 in direct contact with said burn wound 60; and
  securing the bandage 10 in position over the burn wound 60 with the adhesive material disposed on the first side of the second layer 15 of the bandage 10.

This embodiment can be further enhanced wherein the non-flat, heat-dissipation-enhancing surface topography 5 includes a plurality of heat-dissipation-enhancing protrusions 7 (also, see, e.g., FIGS. 10A-10N), said protrusions selected from the group consisting of cone-like protrusions, half-dome-like protrusions, and pyramid-like protrusions. In variations, the plurality of heat-dissipation-enhancing protrusions 7 (also see, e.g., FIGS. 10A-10N) are disposed in rows on the first layer 5, the positioning of every row with respect to its adjacent row(s) is selected from the group consisting of staggered and non-staggered. In yet another variation, at least one heat-dissipation-enhancing protrusion 7 has a hole 6 disposed from its apex toward the base plane of the thermally conductive metal substrate 5, which aids in the bandage's 10 thermal convection processes because of the added exposed surface area to air. In other variations, the first layer 5 includes a plurality of manufactured aeration holes 6 in the thermally conductive metal substrate 5. In some applications, the at least one heat-dissipation-enhancing protrusion 7 with a hole 6 disposed from its apex toward the base plane of the thermally conductive metal substrate 5 has its hole extending all the way through the thermally conductive metal substrate 5. In some cases, the hole 6 disposed in at least one heat-dissipation-enhancing protrusion 7 has a diameter that is narrower toward the second surface of the first layer 5 and wider toward the first surface of the first layer, which both aids in the thermal-convection properties of the substrate 5 and is formed by way of a two-step manufacturing stamping process wherein the main protrusion 7 are formed by a first stamping of the substrate 5 from the first surface toward the second surface, then a second stamping/punching at the apex of the formed protrusions 7 toward the first surface of the substrate 5 to form the openings 6. In some other cases, the holes 6 in the formed protrusions 7 are cylindrical in shape, maintaining approximately the same diameter along the length of the hole 6.

This embodiment can be enhanced wherein the material in the thermally conductive metal substrate 5 is comprised of an aluminum alloy containing at least 92% aluminum and about 5% magnesium.

This embodiment can be enhanced wherein the aluminum alloy used in the first layer 5 is annealed by a process comprised of the steps of:
  Subjecting the aluminum alloy to a temperature in the range of 775° C. to 900° C.; and
  Either subjecting the annealed aluminum alloy to furnace cooling or allowing the aluminum alloy to naturally cool; that is, non-furnace cool. It should be noted, however, that the natural cooling step results in substantially removing any strain hardening of the aluminum alloy and ensuring that the re-crystallization of the aluminum alloy results in substantially uniform grain growth and directional orientation.

This embodiment can be enhanced wherein the bandage further comprises a thermochromic indicator member 45, wherein:
  The thermochromic indicator member 45 is in thermal communication 5A with a burn wound via the first layer 5, and
  The thermochromic indicator member 45 is comprised of material calibrated to indicate to a user when a burn on which the bandage 10 is applied is still too warm for safe removal of said bandage, based on a predetermined threshold, and indicate to a user when a burn has cooled to at least a predetermined threshold such that the bandage 10 can be safely removed and/or changed-out for a new medical dressing.

This embodiment can be enhanced wherein the thermochromic indicator member 45 provides color-based user indications as to the thermal status of the burn to which the bandage 10 is applied.

This embodiment can be enhanced wherein the thermochromic indicator member 45 provides icon-based user indications as to the thermal status of the burn to which the bandage 10 is applied.

This embodiment can be enhanced wherein the thermochromic indicator member 40, 45, 70, 80, 85 is comprised of material selected from the group consisting of thermochromic liquid crystals, leuco dyes, and thermochromic inks.

This embodiment can be enhanced by further comprising the steps of:
  Observing the thermochromic indicator member 45;
  If the thermochromic indicator member 45 indicates that the burn wound 60 is too warm, then continuing the application of the bandage 10 on the burn wound 60 to further cooling of the burn wound 60;
  If the thermochromic indicator member 45 indicates that the burn wound 60 has cooled sufficiently, then removing the bandage 10 from the burn wound 60 and applying a different medical dressing to the burn wound 60; and
  Repeating the previous steps as necessary until the bandage 10 has been removed from the burn wound 60.

This embodiment can be enhanced wherein the different medical dressing referred to above is any one or combination of dressings selected from the group consisting of medicinal compounds, therapeutic compounds, and sterile gauze-based or cotton-based bandages.

This embodiment can be further enhanced wherein the form factor is adapted to facilitate bandage 10 application to a part of a human body selected from the group consisting of finger, thumb, toe, elbow, wrist, knee, ankle, foot, hand palm, and face. In variations, the form factor is of a shape selected from the group consisting of rectangle, square, rounded-corner rectangle, circle, oval, triangle, rounded-corner triangle, and continuous-strip roll.

This embodiment can be further enhanced wherein the second layer 15 is substantially comprised of perforated 1527-ENP ethylene vinyl acetate (EVA).

This embodiment can be enhanced by further comprising the step of subjecting the exposed aluminum substrate 5 of the applied bandage 10 to forced-air cooling in order to speed cooling of the burn wound 60.

Alternative Embodiments and Other Variations

The various embodiments and variations thereof described herein (including the appended claims) and/or illustrated in the accompanying Figures are merely exemplary and are not meant to limit the scope of the inventive disclosure. It should be appreciated that numerous variations of the invention have been contemplated as would be obvious to one of ordinary skill in the art with the benefit of this disclosure.

Hence, those ordinarily skilled in the art will have no difficulty devising myriad obvious variations and improvements to the invention, all of which are intended to be encompassed within the scope of the description and Figures herein.

What is claimed is:
1. A bandage for a burn wound, comprising:
a first layer, substantially comprised of a thin thermally conductive metal substrate, having a first surface and a second surface,
  wherein said metal substrate's first surface has a profile, when viewed from a side, that is substantially flat and adapted to make direct contact with said burn wound,
  wherein most of said metal substrate's second surface has a non-flat, heat-dissipation-enhancing surface topography, when viewed from the side, that rises above a base plane of said thermally conductive metal substrate, and is adapted to be directly exposed to air, wherein said non-flat, heat-dissipation-enhancing surface topography includes a plurality of heat-dissipation-enhancing protrusions, said protrusions selected from the group consisting of substantially cone shaped protrusions, substantially half-dome shaped protrusions, and substantially pyramid shaped protrusions, and wherein at least one heat-dissipation-enhancing protrusion has a hole disposed from its apex toward the base plane of said thermally conductive metal substrate.

2. A bandage for a burn wound, comprising:

a first layer, substantially comprised of a thin thermally conductive metal substrate, having a first surface and a second surface, wherein said metal substrate's first surface has a profile, when viewed from a side, that is substantially flat and adapted to make direct contact with said burn wound, wherein most of said metal substrate's second surface has a non-flat, heat-dissipation-enhancing surface topography, when viewed from the side, that rises above a base plane of said thermally conductive metal substrate, and is adapted to be directly exposed to air, and wherein said first layer includes a plurality of manufactured aeration holes in said thermally conductive metal substrate.

3. The bandage of claim 1, wherein said at least one heat-dissipation-enhancing protrusion with a hole disposed from its apex toward the base plane of said thermally conductive metal substrate has its hole extending all the way through said thermally conductive metal substrate.

4. The bandage of claim 3, wherein said hole disposed in at least one heat-dissipation-enhancing protrusion has a diameter that is narrower toward said second surface of said first layer and wider toward said first surface of said first layer.

5. The bandage of claim 3, wherein said hole disposed in at least one heat-dissipation-enhancing protrusion has a diameter that is substantially the same size along the length of said hole.

6. A bandage for a burn wound, comprising:

a first layer, substantially comprised of a thin thermally conductive metal substrate, having a first surface and a second surface, wherein said metal substrate's first surface has a profile, when viewed from a side, that is substantially flat and adapted to make direct contact with said burn wound, and wherein most of said metal substrate's second surface has a non-flat, heat-dissipation-enhancing surface topography, when viewed from the side, that rises above a base plane of said thermally conductive metal substrate, and is adapted to be directly exposed to air;

a second outer layer, substantially comprised of a substantially polymeric material, said second layer having a first surface and a second surface, wherein said second outer layer's first surface is adapted to mate with and cover at least two perimeter edges of said second surface of said first layer, but also leaving most of said first layer's second surface uncovered and exposed to the air, wherein said second layer extends beyond said at least two perimeter edges of said first layer, wherein said at least two perimeter edges of said first layer are bonded to a portion of the first surface of said second layer, wherein a remainder of the first surface of said second outer layer is substantially coated with a non-toxic adhesive material adapted for use on user skin, and wherein said first and second layers are sized and shaped to a form factor that is adapted for use on one or more areas of a user body; and a thermochromic indicator member, wherein said thermochromic indicator member is in thermal communication with said burn wound via said first layer, and wherein said thermochromic indicator member is comprised of material calibrated to:

indicate to a user when a burn on which said bandage is applied is still too warm for safe removal of said bandage, based on a predetermined threshold, and indicate to a user when a burn has cooled to at least a predetermined threshold such that said bandage can be safely removed and/or changed-out for a new medical dressing.

7. The bandage of claim 6, wherein said thermochromic indicator member provides color-based user indications as to the thermal status of the burn to which said bandage is applied.

8. The bandage of claim 6, wherein said thermochromic indicator member provides icon-based user indications as to the thermal status of the burn to which said bandage is applied.

9. The bandage of claim 6, wherein said thermochromic indicator member is comprised of material selected from the group consisting of thermochromic liquid crystals, leuco dyes, and thermochromic inks.

10. A method of making a bandage for a burn wound, comprising: providing a first layer, substantially comprised of a thin thermally conductive metal substrate, having a first surface and a second surface, wherein said metal substrate's first surface has a profile, when viewed from the side, that is substantially flat and adapted to make direct contact with a burn wound, and wherein most of said metal substrate's second surface has a non-flat, heat-dissipation-enhancing surface topography, when viewed from the side, that rises above the base plane of said thermally conductive metal substrate, and is adapted to be directly exposed to air.

11. The method of claim 10, wherein said thermally conductive metal substrate is substantially comprised of a metal selected from the group consisting of aluminum, silver, gold, copper, magnesium, tungsten, platinum, and a metal alloy substantially based on any other aforementioned metals.

* * * * *